United States Patent
Searle et al.

(10) Patent No.: US 10,625,017 B2
(45) Date of Patent: Apr. 21, 2020

(54) WIRELESS COMMUNICATION FOR ON-BODY MEDICAL DEVICES

(71) Applicant: Becton, Dickinson and Company, Franklin Lakes, NJ (US)

(72) Inventors: Gary Searle, Norfolk, MA (US); Deborah Burns, Westford, MA (US); Bruce Burns, Westford, MA (US); David Mason, Newburyport, MA (US); Charles Hwang, Wellesley, MA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 116 days.

(21) Appl. No.: 15/457,272

(22) Filed: Mar. 13, 2017

(65) Prior Publication Data

US 2017/0281864 A1   Oct. 5, 2017

Related U.S. Application Data

(62) Division of application No. 14/381,949, filed as application No. PCT/US2013/029145 on Mar. 5, 2013, now Pat. No. 9,623,173.

(Continued)

(51) Int. Cl.
- *A61M 5/142* (2006.01)
- *G06F 19/00* (2018.01)
- *A61M 5/168* (2006.01)

(52) U.S. Cl.
CPC ...... *A61M 5/14248* (2013.01); *A61M 5/1684* (2013.01); *A61M 5/16831* (2013.01);
(Continued)

(58) Field of Classification Search
CPC ......... A61M 2005/14252; A61M 2005/14268; A61M 2205/18; A61M 2205/3561; A61M 2205/3569; A61M 2205/3576; A61M 2205/3592; A61M 2205/50; A61M 2205/502; A61M 2205/581; A61M 2205/582; A61M 2205/583;
(Continued)

(56) References Cited

U.S. PATENT DOCUMENTS

| 4,714,462 A | 12/1987 | Didomenico |
| 5,858,001 A | 1/1999 | Tsals et al. |

(Continued)

FOREIGN PATENT DOCUMENTS

| DE | 102014003249 A1 | 9/2015 |
| JP | 2007535366 | 12/2007 |

(Continued)

*Primary Examiner* — Quynh-Nhu H. Vu
(74) *Attorney, Agent, or Firm* — Dickinson Wright PLLC

(57) ABSTRACT

Apparatus, systems and methods for the wireless communication of medical devices in an on-body fluid delivery system are disclosed. A system for on-body fluid delivery includes a primary patch pump adapted to attach a first infusion cannula to a user and to perform a plurality of primary patch pump functions, and a secondary patch pump adapted to attach a second infusion cannula to a user. The secondary patch pump is further adapted to perform a plurality of secondary patch pump functions substantially similar to the plurality of primary patch pump functions if an error condition associated with the primary patch pump is determined.

12 Claims, 27 Drawing Sheets

Related U.S. Application Data

(60) Provisional application No. 61/606,929, filed on Mar. 5, 2012.

(52) U.S. Cl.
CPC ...... *G06F 19/3418* (2013.01); *G06F 19/3468* (2013.01); *A61M 2005/14252* (2013.01); *A61M 2005/14268* (2013.01); *A61M 2205/18* (2013.01); *A61M 2205/3561* (2013.01); *A61M 2205/3569* (2013.01); *A61M 2205/3576* (2013.01); *A61M 2205/3592* (2013.01); *A61M 2205/50* (2013.01); *A61M 2205/502* (2013.01); *A61M 2205/581* (2013.01); *A61M 2205/582* (2013.01); *A61M 2205/583* (2013.01); *A61M 2205/8212* (2013.01); *A61M 2209/01* (2013.01)

(58) Field of Classification Search
CPC ...... A61M 2205/8212; A61M 2209/01; A61M 5/14248; A61M 5/16831; A61M 5/1684; G06F 19/00; G06F 19/3418; G06F 19/3468
See application file for complete search history.

(56) References Cited

U.S. PATENT DOCUMENTS

| | | | |
|---|---|---|---|
| 5,858,005 A | 1/1999 | Kriesel | |
| 5,957,895 A | 9/1999 | Sage et al. | |
| 6,074,369 A | 6/2000 | Sage et al. | |
| 6,485,461 B1 | 11/2002 | Mason et al. | |
| 6,551,276 B1 | 4/2003 | Mann et al. | |
| 6,554,822 B1 | 4/2003 | Holschneider et al. | |
| 6,589,229 B1 | 7/2003 | Connelly et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,673,440 B2 | 1/2004 | Douglas et al. | |
| 6,692,457 B2 | 2/2004 | Flaherty | |
| 6,699,218 B2 | 3/2004 | Flaherty et al. | |
| 6,723,072 B2 | 4/2004 | Flaherty et al. | |
| 6,740,059 B2 | 5/2004 | Flaherty | |
| 6,749,587 B2 | 6/2004 | Flaherty | |
| 6,768,425 B2 | 7/2004 | Flaherty et al. | |
| 6,830,558 B2 | 12/2004 | Flaherty et al. | |
| 6,852,103 B2 | 2/2005 | Fowles et al. | |
| 6,852,104 B2 | 2/2005 | Blomquist | |
| 6,960,192 B1 | 11/2005 | Flaherty et al. | |
| 7,018,360 B2 | 3/2006 | Flaherty et al. | |
| 7,029,455 B2 | 4/2006 | Flaherty | |
| 7,052,251 B2 | 5/2006 | Nason et al. | |
| 7,109,878 B2 | 9/2006 | Mann et al. | |
| 7,128,727 B2 | 10/2006 | Flaherty et al. | |
| 7,137,964 B2 | 11/2006 | Flaherty | |
| 7,144,384 B2 | 12/2006 | Gorman et al. | |
| 7,226,278 B2 | 6/2007 | Nason et al. | |
| 7,303,549 B2 | 12/2007 | Flaherty et al. | |
| 7,455,663 B2 | 11/2008 | Bikovsky | |
| 7,530,964 B2 | 5/2009 | Lavi et al. | |
| 7,628,770 B2 | 12/2009 | Ethelfeld | |
| 7,682,338 B2 | 3/2010 | Griffin | |
| 7,704,226 B2 | 4/2010 | Mueller et al. | |
| 7,713,240 B2 | 5/2010 | Istoc et al. | |
| 7,713,262 B2 | 5/2010 | Adams et al. | |
| 7,736,338 B2 | 6/2010 | Kavazov et al. | |
| 7,736,344 B2 | 6/2010 | Moberg et al. | |
| 7,771,391 B2 | 8/2010 | Carter | |
| 7,771,412 B2 | 8/2010 | Anderson et al. | |
| 7,780,636 B2 | 8/2010 | Radmer et al. | |
| 7,789,857 B2 | 9/2010 | Moberg et al. | |
| 7,794,434 B2 | 9/2010 | Mounce et al. | |
| 7,811,262 B2 | 10/2010 | Moberg et al. | |
| 7,828,764 B2 | 11/2010 | Moberg et al. | |
| 7,887,505 B2 | 2/2011 | Flaherty | |
| 7,905,868 B2 | 3/2011 | Moberg et al. | |
| 7,955,297 B2 | 6/2011 | Radmer et al. | |
| 7,955,305 B2 | 6/2011 | Moberg et al. | |
| 7,981,085 B2 | 7/2011 | Ethelfeld | |
| 8,021,334 B2 | 9/2011 | Shekalim | |
| 8,062,253 B2 | 11/2011 | Nielsen et al. | |
| 8,114,064 B2 | 2/2012 | Alferness et al. | |
| 8,118,782 B2 | 2/2012 | Remde | |
| 8,137,314 B2 | 3/2012 | Mounce et al. | |
| 8,162,923 B2 | 4/2012 | Adams et al. | |
| 8,172,807 B2 | 5/2012 | Dikeman et al. | |
| 8,187,228 B2 | 5/2012 | Bikovsky | |
| 8,202,250 B2 | 6/2012 | Stutz | |
| 8,221,385 B2 | 7/2012 | Estes et al. | |
| 8,226,606 B2 | 7/2012 | Adams et al. | |
| 8,226,607 B2 | 7/2012 | Carter et al. | |
| 8,257,324 B2 | 9/2012 | Prausnitz et al. | |
| 8,262,614 B2 | 9/2012 | Freeman et al. | |
| 8,267,921 B2 | 9/2012 | Yodfat et al. | |
| 8,277,415 B2 | 10/2012 | Mounce et al. | |
| 8,343,092 B2 | 1/2013 | Rush et al. | |
| 8,512,276 B2 | 8/2013 | Talbot et al. | |
| 8,512,288 B2 | 8/2013 | Moberg et al. | |
| 8,540,673 B2 | 9/2013 | Hines et al. | |
| 8,641,671 B2 | 2/2014 | Michaud et al. | |
| 2002/0040208 A1 | 4/2002 | Flaherty et al. | |
| 2003/0055380 A1 | 3/2003 | Flaherty | |
| 2004/0010207 A1 | 1/2004 | Flaherty et al. | |
| 2004/0059316 A1 | 3/2004 | Smedegaard | |
| 2004/0068230 A1 | 4/2004 | Estes et al. | |
| 2004/0078028 A1 | 4/2004 | Flaherty et al. | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0153032 A1 | 8/2004 | Garibotto et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0021005 A1 | 1/2005 | Flaherty et al. | |
| 2005/0022274 A1 | 1/2005 | Campbell et al. | |
| 2005/0065760 A1 | 3/2005 | Murtfeldt et al. | |
| 2005/0090808 A1 | 4/2005 | Malave et al. | |
| 2005/0171512 A1 | 8/2005 | Flaherty | |
| 2005/0182366 A1 | 8/2005 | Vogt et al. | |
| 2005/0215982 A1 | 9/2005 | Malave et al. | |
| 2005/0222645 A1 | 10/2005 | Malave et al. | |
| 2005/0238507 A1 | 10/2005 | Diianni et al. | |
| 2006/0041229 A1 | 2/2006 | Garibotto et al. | |
| 2006/0074381 A1 | 4/2006 | Malave et al. | |
| 2006/0178633 A1 | 8/2006 | Garibotto et al. | |
| 2006/0282290 A1 | 12/2006 | Flaherty et al. | |
| 2007/0016170 A1 | 1/2007 | Kovelman | |
| 2007/0021733 A1 | 1/2007 | Hansen et al. | |
| 2007/0066956 A1 | 3/2007 | Finkel | |
| 2007/0073229 A1 | 3/2007 | Gorman et al. | |
| 2007/0118405 A1 | 5/2007 | Campbell et al. | |
| 2007/0124002 A1 | 5/2007 | Estes et al. | |
| 2007/0228071 A1* | 10/2007 | Kamen | G05D 7/0647 222/52 |
| 2007/0250007 A1 | 10/2007 | Shekalim | |
| 2008/0051697 A1 | 2/2008 | Mounce et al. | |
| 2008/0051698 A1 | 2/2008 | Mounce et al. | |
| 2008/0051765 A1 | 2/2008 | Mounce | |
| 2008/0097327 A1 | 4/2008 | Bente et al. | |
| 2008/0119707 A1 | 5/2008 | Stafford | |
| 2008/0132842 A1 | 6/2008 | Flaherty | |
| 2008/0160492 A1 | 7/2008 | Campbell et al. | |
| 2009/0012473 A1 | 1/2009 | Stettler et al. | |
| 2009/0247982 A1 | 10/2009 | Krulevitch et al. | |
| 2009/0254037 A1 | 10/2009 | Bryant, Jr. et al. | |
| 2010/0137790 A1 | 6/2010 | Yodfat | |
| 2010/0145303 A1 | 6/2010 | Yodfat et al. | |
| 2010/0292645 A1 | 11/2010 | Hungerford et al. | |
| 2011/0021978 A1 | 1/2011 | Martin et al. | |
| 2011/0047499 A1* | 2/2011 | Mandro | A61M 5/142 715/780 |
| 2011/0105955 A1 | 5/2011 | Yudovsky et al. | |

(56) References Cited

U.S. PATENT DOCUMENTS

| | | |
|---|---|---|
| 2011/0132401 A1 | 6/2011 | Shumey et al. |
| 2011/0218495 A1* | 9/2011 | Remde .............. A61M 5/14248 |
| | | 604/151 |
| 2012/0022645 A1 | 1/2012 | Burke |
| 2012/0095311 A1 | 4/2012 | Ramey et al. |
| 2012/0130312 A1 | 5/2012 | Mernoe et al. |
| 2012/0266251 A1 | 10/2012 | Birtwhistle et al. |
| 2013/0039239 A1 | 2/2013 | Lin |
| 2013/0253472 A1* | 9/2013 | Cabiri ............... A61M 5/14248 |
| | | 604/506 |
| 2014/0052096 A1 | 2/2014 | Searle et al. |

FOREIGN PATENT DOCUMENTS

| | | |
|---|---|---|
| JP | 2010534085 | 11/2010 |
| WO | WO-2007056592 A2 | 5/2007 |
| WO | WO-2009109344 A1 | 9/2009 |
| WO | WO-2009112513 A1 | 9/2009 |

* cited by examiner

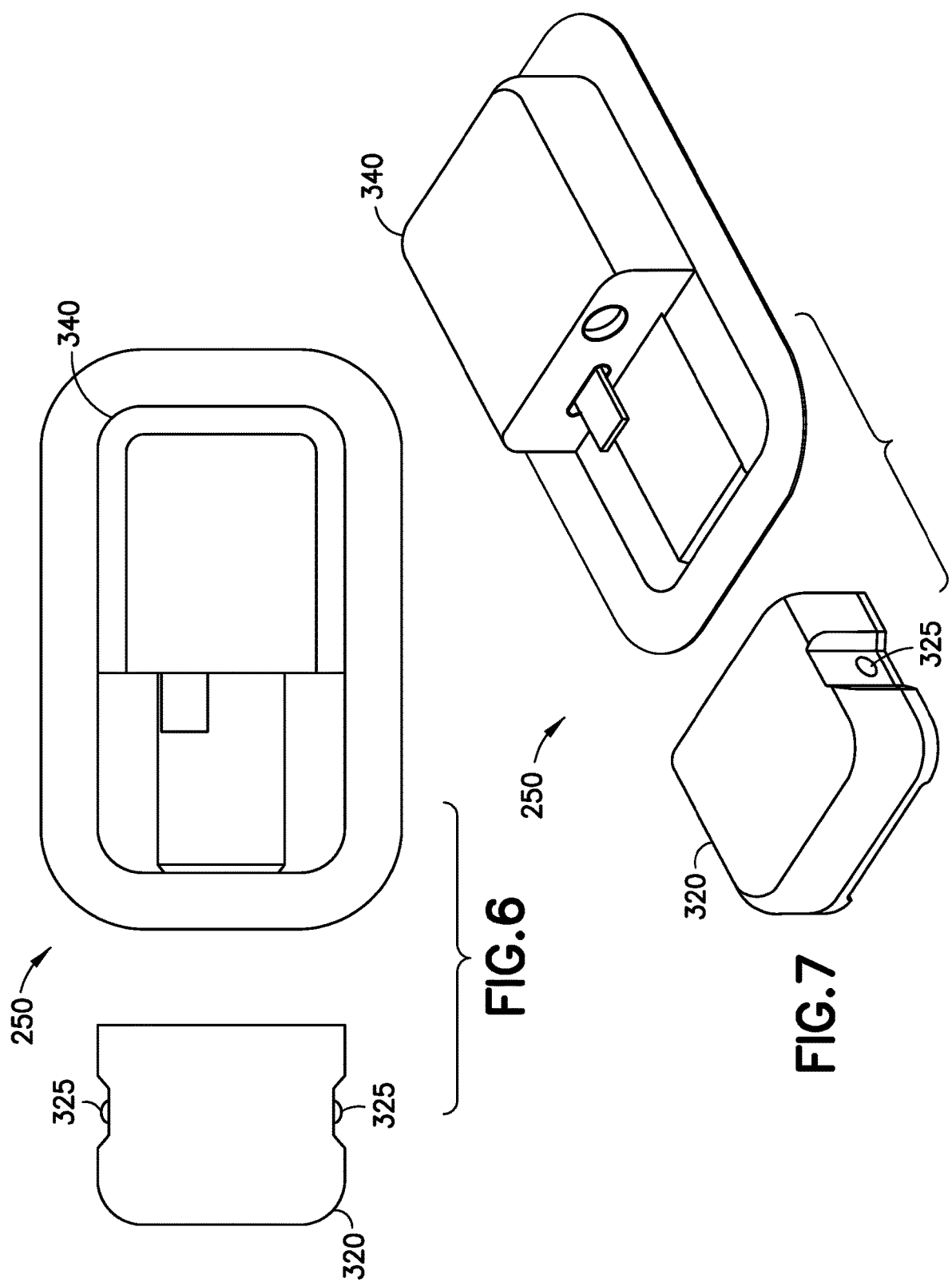

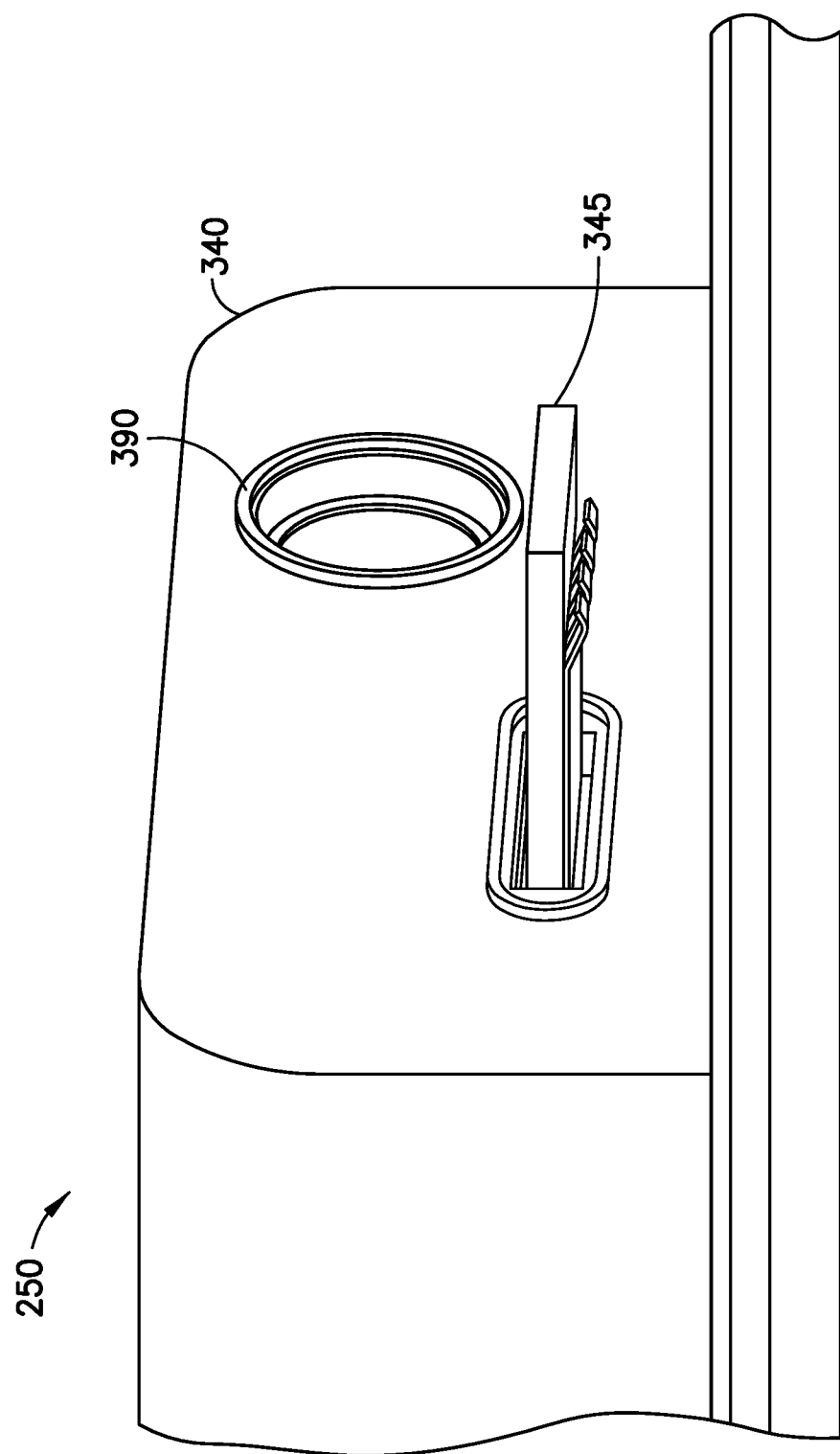

| STATE | DEVICES IN MEDICAL THERAPEUTIC / DIAGNOSTIC SYSTEM | | | SYSTEM OPERATION |
|---|---|---|---|---|
| | PATCH PUMP 1 (PP1) | PATCH PUMP 2 (PP2) | USER INTERFACE 1 (UI1) (FULL FEATURE) | USER INTERFACE 2 (UI2) (BOLUS & ALARMS) | |
| 1 | IN SYSTEM | | | | PP1 WAS INITIALLY PAIRED TO UI1, WHICH SYNCHRONIZED THE "SLEEP", "WAKE", "SNIFF" CYCLE OF BOTH DEVICES. IN THE ABSENCE OF UI1, PP1 WILL WAKE, CONDUCT SELF-DIAGNOSTICS, SNIFF FOR THE UI1, AND THEN RETURN TO SLEEP. PP1 CONTINUES TO PROVIDE BASAL INFUSION AT THE RATE PREVIOUSLY TRANSMITTED FROM THE UI. BOLUS DELIVERY CAN BE INITIATED MANUALLY BY THE USER VIA THE PUSH-BUTTONS ON PP1 |
| 2 | IN SYSTEM | | IN SYSTEM | | PP1 WAS INITIALLY PAIRED TO UI1, WHICH SYNCHRONIZED THE "SLEEP", "WAKE", "SNIFF" CYCLE OF BOTH DEVICES. PP1 WILL WAKE, CONDUCT SELF-DIAGNOSTICS, SNIFF, RECOGNIZE UI1, TRANSFER THE INFUSION PROFILE UPDATE WHICH OCCURRED SINCE THE PREVIOUS UPDATE WAS TRANSMITTED, RECEIVE INFUSION COMMANDS, e.g. BOLUS DOSE REQUIREMENT OR BASAL RATE ADJUSTMENT, DELIVER THE BOLUS DOSE AND MAKE ANY ADJUSTMENTS TO THE BASAL RATE, TRANSMIT CONFIRMATION OF DELIVERY AND / OR ADJUSTMENT, AND THEN RETURN TO SLEEP |
| 3 | IN SYSTEM | | IN SYSTEM | IN SYSTEM | PP1 WAS INITIALLY PAIRED TO UI1, AND UI2 WAS ALSO PAIRED TO UI1, WHICH SYNCHRONIZED THE "SLEEP", "WAKE", "SNIFF" CYCLE OF ALL THREE DEVICES. PP1 WILL WAKE, CONDUCT SELF-DIAGNOSTICS, SNIFF, RECOGNIZE BOTH UI1 AND UI2, PP1 WILL TRANSFER TO BOTH UIs THE INFUSION PROFILE UPDATE WHICH OCCURRED SINCE THE PREVIOUS UPDATE WAS TRANSMITTED. HOWEVER, IN THE PRESENCE OF BOTH UIs, PP1 WILL ONLY RECEIVE INFUSION COMMANDS FROM UI1, e.g. BOLUS DOSE REQUIREMENT OR BASAL RATE ADJUSTMENT. FOLLOWING THE DELIVERY OF THE BOLUS DOSE AND ANY REQUIRED ADJUSTMENTS TO THE BASAL RATE, PP1 WILL TRANSMIT CONFIRMATION OF DELIVERY AND / OR ADJUSTMENT, AND THEN RETURN TO SLEEP |

| | | | |
|---|---|---|---|
| 4 | IN SYSTEM | | PP1 WAS INITIALLY PAIRED TO UI1, AND UI2 WAS ALSO PAIRED TO UI1, WHICH SYNCHRONIZED THE "SLEEP", "WAKE", "SNIFF" CYCLE OF ALL THREE DEVICES. PP1 WILL WAKE, CONDUCT SELF-DIAGNOSTICS, SNIFF, RECOGNIZE ONLY UI2. IN THE ABSENCE OF UI1, PP1 WILL TRANSFER TO UI2 THE INFUSION PROFILE UPDATE WHICH OCCURRED SINCE THE PREVIOUS UPDATE WAS TRANSMITTED. SINCE UI2 CAN ONLY PROVIDE A SINGLE INFUSION COMMAND, i.e. A BOLUS DOSE REQUIREMENT, PP1 WILL RECEIVE THE BOLUS DOSE COMMAND FROM UI2, AND FOLLOWING THE DELIVERY, PP1 WILL TRANSMIT CONFIRMATION OF DELIVERY TO UI2, AND THEN RETURN TO SLEEP. EITHER UI2 OR PP1 WILL UPDATE UI1, THE NEXT TIME UI1 IS RECOGNIZED AS THE DEVICES IN THE SYSTEM CONTINUE TO WAKE, SNIFF, AND SLEEP |
| 5 | IN SYSTEM | IN SYSTEM | PP1 WAS INITIALLY PAIRED TO UI1, AND PP2 WAS ALSO PAIRED SEPARATELY TO UI1, WHICH SYNCHRONIZED THE "SLEEP", "WAKE", "SNIFF" CYCLE OF ALL THREE DEVICES. IN THE ABSENCE OF UI1, PP1 WILL WAKE, CONDUCT SELF-DIAGNOSTICS, SNIFF FOR UI1 AND ANY OTHER DEVICES TO WHICH PP1 HAS BEEN PAIRED, TRANSFER TO PP2 THE INFUSION PROFILE UPDATE WHICH OCCURRED SINCE THE PREVIOUS UPDATE WAS TRANSMITTED, AND THEN RETURN TO SLEEP. BOLUS DELIVERY CAN BE PROVIDED MANUALLY BY THE USER. IF A MANUAL BOLUS COMMAND IS PROVIDED BY THE USER TO PP1, THEN UPON WAKING BOTH PP1 AND PP2 WILL REMAIN AWAKE UNTIL THE COMPLETE BOLUS DOSE HAS BEEN DELIVERED. IF THERE IS INSUFFICIENT INSULIN REMAINING IN THE RESERVOIR OF PP1, PP1 WILL COMMUNICATE THE REMAINING REQUIREMENT TO PP2, AND THE BASAL DELIVER RATE. PP2 WILL THEN DEPLOY THE INFUSION CATHETER, DELIVER THE REMAINDER OF THE BOLUS DOSE, AND RETURN TO SLEEP. AFTER RECEIVING CONFIRMATION FROM PP2, PP1 WILL DISABLE ALL INFUSION CAPABILITY AND RETURN TO THE SYNCHRONIZED SLEEP, WAKE, SNIFF CYCLE. PP2 WILL NOW OPERATE AS PP1 IN STATE 1, AND CONTINUE TO PROVIDE BASAL INFUSION, AND MANUALLY ACTUATED, INCREMENTAL BOLUS DOSING. IF UPON WAKING PP2 RECOGNIZES UI1, THEN PP2 WILL UPDATE UI1, AND THEN PP2 AND UI1 WILL OPERATE AS PP1 AND UI1 IN STATE 2. THE CATHETER IN PP1 CAN BE AUTOMATICALLY RETRACTED AND THE ADHESIVE CAN BE AUTOMATICALLY DISSOLVED FROM A COMMAND PROVIDED BY UI1, OR PP1 CAN BE MANUALLY REMOVED FROM THE SKIN SURFACE OF THE USER |

FIG.22B

| STATE | DEVICES | | | SYSTEM OPERATION |
|---|---|---|---|---|
| | IN MEDICAL THERAPEUTIC / DIAGNOSTIC SYSTEM | | | |
| | PATCH PUMP 1 (PP1) | PATCH PUMP 2 (PP2) | USER INTERFACE 1 (UI1) (FULL FEATURE) | USER INTERFACE 2 (UI2) (BOLUS & ALARMS) |
| 6 | IN SYSTEM | IN SYSTEM | IN SYSTEM | | PP1 WAS INITIALLY PAIRED TO UI1, AND PP2 WAS ALSO PAIRED SEPARATELY TO UI1, WHICH SYNCHRONIZED THE "SLEEP", "WAKE", "SNIFF" CYCLE OF ALL THREE DEVICES. TOGETHER PP1 AND PP2 WILL WAKE, CONDUCT SELF-DIAGNOSTICS, SNIFF, AND RECOGNIZE UI1. PP1 WILL TRANSFER TO UI1 THE INFUSION PROFILE UPDATE WHICH OCCURRED SINCE THE PREVIOUS UPDATE WAS TRANSMITTED. UI1 WILL TRANSFER TO PP2 THE INFUSION PROFILE UPDATE WHICH OCCURRED SINCE THE PREVIOUS UPDATE WAS TRANSMITTED. PP1 WILL RECEIVE INFUSION COMMANDS FROM UI1, e.g. BOLUS DOSE REQUIREMENT OR BASAL RATE ADJUSTMENT. FOLLOWING THE DELIVERY OF THE BOLUS DOSE AND ANY REQUIRED ADJUSTMENTS TO THE BASAL RATE, PP1 WILL TRANSMIT CONFIRMATION OF DELIVERY AND / OR ADJUSTMENT TO UI1, AND UI1 WILL IN TURN TRANSMIT THE UPDATE TO PP2, AND THEN ALL THREE DEVICES WILL RETURN TO SLEEP. IF THERE IS INSUFFICIENT INSULIN REMAINING IN THE RESERVOIR OF PP1 TO COMPLETE THE REQUIRED BOLUS DELIVERY OR CONTINUE BASAL RATE INFUSION, PP1 WILL COMMUNICATE THE REMAINING REQUIREMENT TO UI1. AFTER RECEIVING CONFIRMATION FROM UI1, PP1 WILL DISABLE ALL INFUSION CAPABILITY AND RETURN TO THE SYNCHRONIZED SLEEP, WAKE, SNIFF CYCLE. UI1 WILL THEN TRANSFER THE REMAINING BOLUS REQUIREMENT OR BASAL RATE TO PP2. PP2 WILL THEN DEPLOY THE INFUSION CATHETER, DELIVER THE REMAINDER OF THE BOLUS DOSE OR CONTINUE AT THE BASAL RATE, TRANSMIT CONFIRMATION OF THE SAME, AND RETURN TO SLEEP. PP2 WILL NOW OPERATE AS PP1 IN STATE 2 |

| FIG.23A |
|---|
| FIG.23B |
| FIG.23C |

PP1 WAS INITIALLY PAIRED TO UI1, PP2 WAS PAIRED SEPARATELY TO UI1, AND UI2 WAS ALSO PAIRED TO UI1, WHICH SYNCHRONIZED THE "SLEEP", "WAKE", "SNIFF" CYCLE OF ALL FOUR DEVICES. TOGETHER PP1 AND PP2 WILL WAKE, CONDUCT SELF-DIAGNOSTICS, SNIFF, AND RECOGNIZE BOTH UI1 AND UI2. PP1 WILL TRANSFER TO BOTH UIs THE INFUSION PROFILE UPDATE WHICH OCCURRED SINCE THE PREVIOUS UPDATE WAS TRANSMITTED. UI1 WILL TRANSFER TO PP2 THE INFUSION PROFILE UPDATE WHICH OCCURRED SINCE THE PREVIOUS UPDATE WAS TRANSMITTED. IN THE PRESENCE OF BOTH UIs, PP1 WILL ONLY RECEIVE INFUSION COMMANDS FROM UI1, e.g. BOLUS DOSE REQUIREMENT OR BASAL RATE ADJUSTMENT. FOLLOWING THE DELIVERY OF THE BOLUS DOSE AND ANY REQUIRED ADJUSTMENTS TO THE BASAL RATE, PP1 WILL TRANSMIT CONFIRMATION OF DELIVERY AND/OR ADJUSTMENT TO BOTH UI1 AND UI2, AND UI1 WILL IN TURN TRANSMIT THE UPDATE TO PP2, AND THEN ALL FOUR DEVICES WILL RETURN TO SLEEP. IF THERE IS INSUFFICIENT INSULIN REMAINING IN THE RESERVOIR OF PP1 TO COMPLETE THE REQUIRED BOLUS DELIVERY OR CONTINUE BASAL RATE INFUSION, PP1 WILL COMMUNICATE THE REMAINING REQUIREMENT TO UI1. AFTER RECEIVING CONFIRMATION FROM UI1, PP1 WILL DISABLE ALL INFUSION CAPABILITY AND RETURN TO THE SYNCHRONIZED SLEEP, WAKE, SNIFF CYCLE. UI1 WILL THEN TRANSFER THE REMAINING BOLUS REQUIREMENT OR BASAL RATE TO PP2. PP2 WILL THEN DEPLOY THE INFUSION THEN DEPLOY THE INFUSION CATHETER, DELIVER THE REMAINDER OF THE BOLUS DOSE OR CONTINUE AT THE BASAL RATE, TRANSMIT CONFIRMATION OF THE SAME AND RESUMPTION OF BASAL DELIVERY, AND ALL FOUR DEVICES WILL RETURN TO SLEEP. PP2 WILL NOW OPERATE AS PP1 IN STATE 3

| 7 | IN SYSTEM | IN SYSTEM | IN SYSTEM | IN SYSTEM |

FIG. 23B

| 8 | IN SYSTEM | IN SYSTEM | IN SYSTEM | PP1 WAS INITIALLY PAIRED TO UI1, PP2 WAS PAIRED SEPARATELY AND UI1, AND UI2 WAS ALSO PAIRED TO UI1, WHICH SYNCHRONIZED THE "SLEEP", "WAKE", "SNIFF" CYCLE OF ALL FOUR DEVICES. TOGETHER PP1 AND PP2 WILL WAKE, CONDUCT SELF-DIAGNOSTICS, SNIFF, AND RECOGNIZE ONLY UI2. PP1 WILL TRANSFER TO UI2 THE INFUSION PROFILE UPDATE WHICH OCCURRED SINCE THE PREVIOUS UPDATE WAS TRANSMITTED. UI2 WILL TRANSFER TO PP2 THE INFUSION PROFILE UPDATE WHICH OCCURRED SINCE THE PREVIOUS UPDATE WAS TRANSMITTED. IN THE ABSENCE OF UI1, PP1 WILL RECEIVE INFUSION COMMANDS FROM UI2 e.g. BOLUS DOSE REQUIREMENT OR BASAL RATE ADJUSTMENT. FOLLOWING THE DELIVERY OF THE BOLUS DOSE AND ANY REQUIRED ADJUSTMENTS TO THE BASAL RATE, PP1 WILL TRANSMIT CONFIRMATION OF DELIVERY AND/OR ADJUSTMENT TO UI2, AND UI2 WILL IN TURN TRANSMIT THE UPDATE TO PP2, AND THEN ALL THREE DEVICES WILL RETURN TO SLEEP. IF THERE IS INSUFFICIENT INSULIN REMAINING IN THE RESERVOIR OF PP1 TO COMPLETE THE REQUIRED BOLUS DELIVERY OR CONTINUE BASAL RATE INFUSION, PP1 WILL COMMUNICATE THE REMAINING REQUIREMENT TO UI2. AFTER RECEIVING CONFIRMATION FROM UI2, PP1 WILL DISABLE ALL INFUSION CAPABILITY AND RETURN TO THE TO THE SYNCHRONIZED SLEEP, WAKE, SNIFF CYCLE. UI2 WILL THEN TRANSFER THE REMAINING BOLUS DOSE REQUIREMENT OR BASAL RATE TO PP2. PP2 WILL DEPLOY THE INFUSION CATHETER, DELIVER THE REMAINDER OF THE BOLUS DOSE OR CONTINUE AT THE BASAL RATE, TRANSMIT CONFIRMATION OF THE SAME AND RESUMPTION OF BASAL DELIVERY, AND ALL THREE DEVICES WILL RETURN TO SLEEP. PP2 WILL NOW OPERATE AS PP1 IN STATE 4. IF UPON WAKING PP2 RECOGNIZES UI1, THEN PP2 AND UI1 WILL OPERATE AS PP1 AND BOTH UIs IN STATE 3, AND EITHER UI2 OR PP2 WILL UPDATE UI1k, THE NEXT TIME UI1 IS RECOGNIZED AS THE DEVICES IN THE SYSTEM CONTINUE TO WAKE, SNIFF, AND SLEEP |

FIG.23C

| | DEVICES IN MEDICAL THERAPEUTIC / DIAGNOSTIC SYSTEM | | | | |
|---|---|---|---|---|---|
| STATE | PATCH PUMP 1 (PP 1) | PATCH PUMP 2 (PP 2) | USER INTERFACE 1 (UI1) (FULL FEATURE) | USER INTERFACE 2 (UI2) (BOLUS & ALARMS) | SYSTEM OPERATION |
| 9 | | | IN SYSTEM | | IF UPON WAKING, UI1 DOES NOT RECOGNIZE A PP, THEN AN ALARM IS PROVIDED TO THE USER |
| 10 | | | | IN SYSTEM | IF UPON WAKING, UI2 DOES NOT RECOGNIZE A PP, THEN AN ALARM IS PROVIDED TO THE USER |
| 11 | | | IN SYSTEM | IN SYSTEM | IF UPON WAKING, BOTH UI1 AND UI2 DO NOT RECOGNIZE A PP, THEN AN ALARM IS PROVIDED TO THE USER |
| 12 | | IN SYSTEM | IN SYSTEM | | PP1 WAS INITIALLY PAIRED TO UI1, AND PP2 WAS ALSO PAIRED SEPARATELY TO UI1, WHICH SYNCHRONIZED THE "SLEEP", "WAKE" "SNIFF" CYCLE OF ALL THREE DEVICES. PP2 WILL WAKE, CONDUCT SELF-DIAGNOSTICS, SNIFF, AND RECOGNIZE ONLY UI1. IN THE ABSENCE OF PP1. UI1 WILL TRANSFER TO PP2 ANY USER UPDATES FOR BOLUS DOSE REQUIREMENT OR BASAL RATE ADJUSTMENT. PP2 WILL THEN DEPLOY THE INFUSION CATHETER, DELIVER THE BOLUS DOSE, TRANSMIT CONFIRMATION OF THE BOLUS DOSE DELIVERY AND RESUMPTION OF BASAL DELIVERY, AND RETURN TO SLEEP. PP2 WILL NOW OPERATE AS PP1 IN STATE 2. UI1 WILL PROVIDE AN ALARM TO ALERT THE USER THAT PP1 IS NO LONGER FUNCTIONING PROPERLY AND SHOULD BE REMOVED. UI1 WILL REMAIN AWAKE FOR TWO CYCLES SNIFFING FOR PP1, FOLLOWING WHICH UI1 WILL RESUME THE SYNCHRONIZED SLEEP, WAKE SNIFF CYCLE (PP1 INTERNAL PROTOCOLS WILL DISABLE ALL INFUSION CAPABILITY ONCE A COMMUNICATION FAILURE IS DETECTED) |

FIG.24A

| FIG.24A |
|---|
| FIG.24B |

FIG.24

| | | | |
|---|---|---|---|
| 13 | IN SYSTEM | | IN SYSTEM | PP1 WAS INITIALLY PAIRED TO UI1, PP2 WAS PAIRED SEPARATELY TO UI1 AND UI2 WAS ALSO PAIRED TO UI1, WHICH SYNCHRONIZED THE "SLEEP", "WAKE", "SNIFF" CYCLE OF ALL FOUR DEVICES. PP2 WILL WAKE, CONDUCT SELF-DIAGNOSTICS, SNIFF, AND RECOGNIZE ONLY UI2. IN THE ABSENCE OF PP1 AND UI1, UI2 WILL TRANSFER TO PP2 ANY USER UPDATES FOR BOLUS DOSE REQUIREMENT. PP2 WILL THEN DEPLOY THE INFUSION CATHETER, DELIVER THE BOLUS DOSE, TRANSMIT CONFIRMATION OF THE BOLUS DOSE DELIVERY AND RESUMPTION OF BASAL DELIVERY, AND RETURN TO SLEEP. PP2 WILL NOW OPERATE AS PP1 IN STATE 3. UI2 WILL PROVIDE AN ALARM TO ALERT THE USER THAT PP1 IS NO LONGER FUNCTIONING PROPERLY AND SHOULD BE REMOVED. UI2 WILL REMAIN AWAKE FOR TWO CYCLES SNIFFING FOR PP1, FOLLOWING WHICH UI WILL RESUME THE SYNCHRONIZED SLEEP, WAKE, SNIFF, CYCLE. (PP1 INTERNAL PROTOCOLS WILL DISABLE ALL INFUSION CAPABILITY ONCE A COMMUNICATION FAILURE IS DETECTED) |
| 14 | IN SYSTEM | IN SYSTEM | IN SYSTEM | PP1 WAS INITIALLY PAIRED TO UI1, PP2 WAS PAIRED SEPARATELY TO UI1, AND UI2 WAS ALSO PAIRED TO UI1, WHICH SYNCHRONIZED THE "SLEEP", "WAKE", "SNIFF" CYCLE OF ALL FOUR DEVICES. PP2 WILL WAKE, CONDUCT SELF-DIAGNOSTICS, SNIFF AND RECOGNIZE ONLY UI1 AND UI2. IN THE ABSENCE OF PP1, UI1 WILL TRANSFER TO PP2 ANY USER UPDATES FOR BOLUS DOSE REQUIREMENT OR BASAL RATE ADJUSTMENT. PP2 WILL THEN DEPLOY THE INFUSION CATHETER, DELIVER THE BOLUS DOSE, TRANSMIT CONFIRMATION OF THE BOLUS DOSE DELIVERY AND RESUMPTION OF BASAL DELIVERY, AND RETURN TO SLEEP. PP2 WILL NOW OPERATE AS PP1 IN STATE 2. UI1 WILL PROVIDE AN ALARM TO ALERT THE USER THAT PP1 IS NO LONGER FUNCTIONING PROPERLY AND SHOULD BE REMOVED. UI1 WILL REMAIN AWAKE FOR TWO CYCLES SNIFFING FOR PP1, FOLLOWING WHICH UI1 WILL RESUME THE SYNCHRONIZED SLEEP, WAKE, SNIFF CYCLE (PP1 INTERNAL PROTOCOL WILL DISABLE ALL INFUSION CAPABILITY ONCE A COMMUNICATION FAILURE IS DETECTED) |

FIG.24B

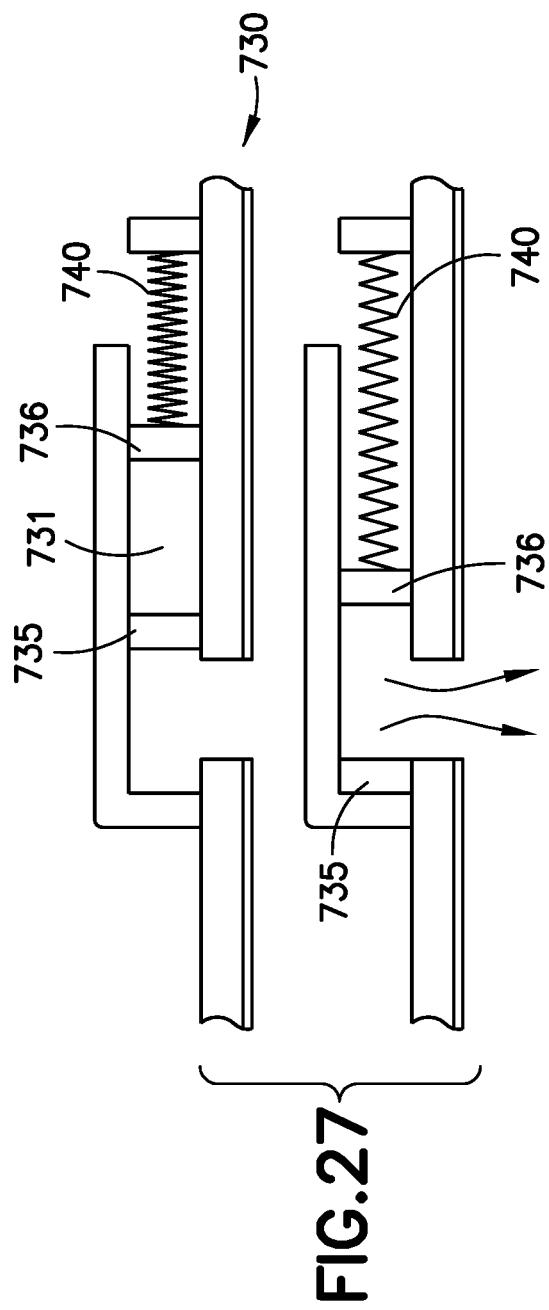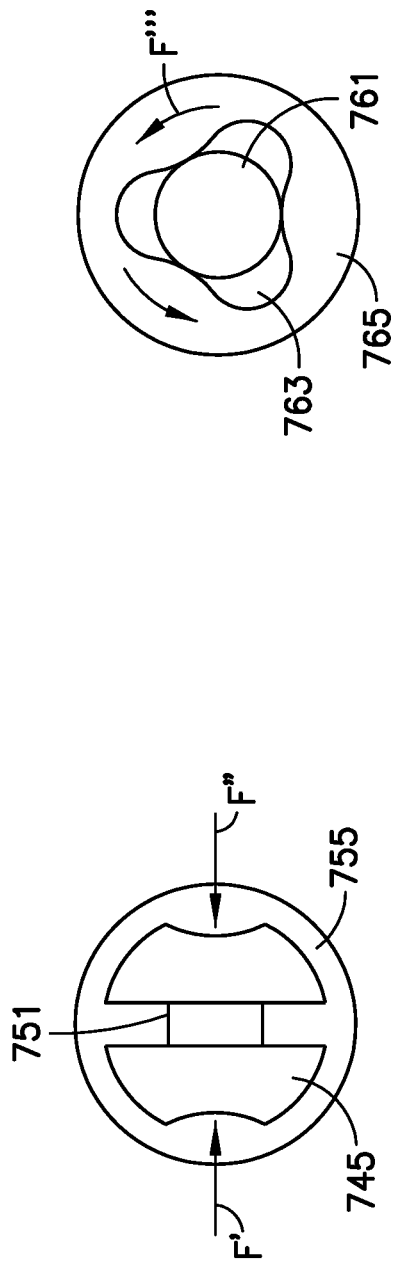

WIRELESS COMMUNICATION FOR ON-BODY MEDICAL DEVICES

RELATED APPLICATIONS

This application is a division of U.S. patent application Ser. No. 14/381,949, filed Aug. 28, 2014, and claims benefit of U.S. Provisional Patent Application No. 61/606,929, filed Mar. 5, 2012, and International Patent Application No. PCT/US2013/029145, filed Mar. 5, 2013, the disclosures of which are incorporated herein by reference in their entireties.

FIELD OF THE INVENTION

The present invention relates generally to wireless communication of medical devices in an on-body fluid delivery system. More specifically, the present invention relates to wireless communication between a remote user interface, a primary on-body medical device, and a preemptive on-body medical device that can be attached to a user's skin simultaneously with the primary on-body medical device.

BACKGROUND OF THE INVENTION

In the contemporary art, a remotely controlled On-Body Medical Device (OBMD) can be used for the continuous infusion of insulin to patients with diabetes. As each OBMD is no longer viable, however, a user must use a user interface (UI) that is paired to the OBMD to deploy and activate an ensuing OBMD.

Moreover, contemporary OBMDs are worn under clothing and attached to the body of the patient. Users typically change their OBMD at regular intervals as part of their routine. For example, a user may change their device every third morning when an OBMD reservoir is almost exhausted. Since most OBMDs are available in only one or two reservoirs sizes, typically the insulin reservoir is not completely exhausted at the start of a day or when the user may be leaving the privacy of their home. This situation creates a dilemma in which the user needs to either waste insulin by prematurely discarding the patch pump or compromise their privacy and discretion by having to change their patch pump in public.

Additionally, electronic clocks utilized in remotely controlled OBMDs with wireless communication, such as real time clocks (RTCs), can vary due to inherent limitations on accuracy and ambient conditions such as temperature or the like. The time delay in the current state of the art for RTCs can be approximately 2 minutes per year, which equates to approximately one second over three days.

Finally, the removal of non-viable contemporary OBMDs from the skin of a user may cause tissue damage. The adhesive can remove portions of the outer surface of the skin that are in contact with the adhesive, making the resulting skin surface more susceptible to infection, and rendering the site less viable as an infusion site, albeit temporarily.

While there are products on the market such that are effective in removing adhesive pads from skin, they are currently packaged as stand-alone products—principally wipes or sprays. This presents several difficulties for the user. For example, it is another device that the user has to keep track of, and it can be difficult to apply if an OBMD is not in the line of sight. Also, many adhesive solvents, such as siloxane are flammable. The contemporary methods for using siloxane expose the solvent to air and the ambient environment, thereby increasing the risk of ignition.

Accordingly, there is a need for a fluid delivery system that provides user discretion, reduces Insulin waste, reduces many use steps in deploying each ensuing OBMD, and allows compliance with prescribed therapy.

Moreover, there is a need for a fluid delivery system to recognize failure and end of service conditions and through active communication with other OBMDs in the system provide uninterrupted therapy. Related to this requirement is a need for a communication method that minimizes power consumption and thereby reduces the power requirements and overall size of the OBMD and UI.

There is also a need for a system for reducing or eliminating the peel force and tissue damage associated with removing the adhesive pad of an OBMD. There is, in addition, a need to have a means of adhesive removal integrated with the infusion device.

SUMMARY OF THE INVENTION

An object of the present invention is to substantially address the above and other concerns, and provide a higher level of discretion when the patient is in the general public, eliminate the waste of drugs associated with discarding partial doses that do not satisfy short term therapeutic requirements, improve ease of use by eliminating the use steps necessary to deploy and activate ensuing OBMDs, provide uninterrupted diagnostics or therapy for a patient, with or without the aid of a user interface, and improve therapeutic compliance by addressing the unmet needs stated above.

Another object of the present invention is to substantially address the timing inaccuracies associated with the RTCs of a UI and an OBMD of a fluid delivery system.

Another object of the present invention is to substantially address reduce or eliminate peel force and tissue damage associated with removing the adhesive pad of an OBMD and decrease the risk of igniting a flammable adhesive solvent when removing the adhesive pad from the skin of a user.

An illustrative embodiment of a system for on-body (e.g., subcutaneous, intradermal, or otherwise) fluid delivery can include a primary patch pump adapted to attach a first infusion cannula to a user, the primary patch pump further adapted to perform a plurality of primary patch pump functions, and a secondary patch pump adapted to attach a second infusion cannula to a user, the secondary patch pump further adapted to perform a plurality of secondary patch pump functions substantially similar to the plurality of primary patch pump functions if an error condition associated with the primary patch pump is determined. The plurality of primary patch pump functions can include at least one of pairing with a primary user interface, being filled with a medicament and primed, deploying a catheter, initiating a bolus dose or basal rate, entering a primary patch pump SLEEP mode, entering a primary patch pump WAKE mode at predetermined primary patch pump WAKE time intervals, and entering a primary patch pump SNIFF mode for up to a predetermined primary patch pump SNIFF time.

In an illustrative method of on-body fluid delivery using a primary user interface communicatively couplable to a primary patch pump, the primary patch pump can include a first reservoir adapted to contain a first fluid, a first catheter, a first pump adapted to infuse the first fluid from the first reservoir through the first catheter, and a first microcontroller adapted to control operations of the first pump.

An illustrative method of on-body fluid delivery can include pairing the primary patch pump to the primary user interface. The primary patch pump can communicate with the primary user interface to determine whether user instructions have been received at the primary user interface. If it is determined that user instructions have been received at the primary user interface, machine instructions can be sent from the primary user interface to the primary patch pump according to the user instructions, and a bolus dose or basal rate can be initiated using the first microcontroller according to the machine instructions.

An illustrative method of on-body fluid delivery can further include checking by the primary patch pump for an error condition. If an error condition is detected by the primary patch pump, a user can be alerted via an alert mechanism and transferring relevant data from the primary patch pump to the primary user interface. If no error condition is detected by the primary patch pump, relevant data can be transferred from the primary patch pump to the primary user interface. The method can return to the step of the primary patch pump communicating with the primary user interface.

An illustrative embodiment of an adhesive removal apparatus can be adhere to skin with an adhesive pad having an adhesive. The adhesive removal apparatus can comprise at least one adhesive solvent reservoir in a base of a body of the device, the at least one adhesive solvent reservoir containing adhesive solvent. The adhesive solvent can be releasable from the at least one adhesive solvent reservoir to act on the adhesive and release the adhesive pad from skin upon the device receiving a release signal.

The adhesive solvent can be encapsulated in the at least one adhesive solvent reservoir. The adhesive solvent can flow through at least one hole in the base of the body of the device when the adhesive solvent is released. The adhesive solvent can be at least partially comprised of siloxane. The adhesive solvent can contact and dissolve the adhesive from the adhesive pad when the adhesive solvent is released. The adhesive solvent can wick to the adhesive pad and dissolve the adhesive from the adhesive pad.

While communications between devices are preferably wireless, a person of ordinary skill in the art would readily appreciate other forms of communication, such as wired communication or a capacitive interface for communication through user tissue, such as skin.

BRIEF DESCRIPTION OF THE DRAWINGS

The various objects, advantages and novel features of the exemplary embodiments of the present invention will be more readily appreciated from the following detailed description when read in conjunction with the appended drawings, in which:

FIG. 6 depicts a top view of an illustrative embodiment of an OBMD of the present invention;

FIG. 7 depicts a perspective view of an illustrative embodiment of an OBMD of the present invention;

FIG. 8 depicts a perspective view of an illustrative embodiment of an OBMD of the present invention;

FIGS. 22A-24B depict a table illustrating fourteen different states and operations for activated medical devices of illustrative embodiments of the fluid delivery system of the present invention.

FIG. 27 depicts an illustrative embodiment of an adhesive removal apparatus of the present invention using a dual stopper mechanism;

FIG. 28 depicts an illustrative embodiment of an adhesive removal apparatus of the present invention using a squeeze chamber;

FIG. 29 depicts an illustrative embodiment of an adhesive removal apparatus of the present invention using a twist chamber.

Throughout the drawing figures, like reference numbers will be understood to refer to like elements, features and structures.

DETAILED DESCRIPTION OF THE EXEMPLARY EMBODIMENTS

Illustrative embodiments of the present invention relate to wireless communication between a remote user interface, a primary On-Body Medical Device, and a preemptive On-Body Medical Device that can be attached to a user's skin simultaneously with the primary On-Body Medical Device or at a later time, prior to the end of life of the On-Body Medical Device.

It is to be understood by a person ordinarily skilled in the art that illustrative embodiments of the invention can contain and/or infuse insulin or any other medicament subcutaneously, intradermally, intramuscularly or otherwise. Throughout the following description systems for subcutaneous infusion are described but it should be understood that subcutaneous infusion is merely exemplary, and embodiments of the invention may deliver fluid intradermally, intramuscularly or otherwise.

Figure 1:
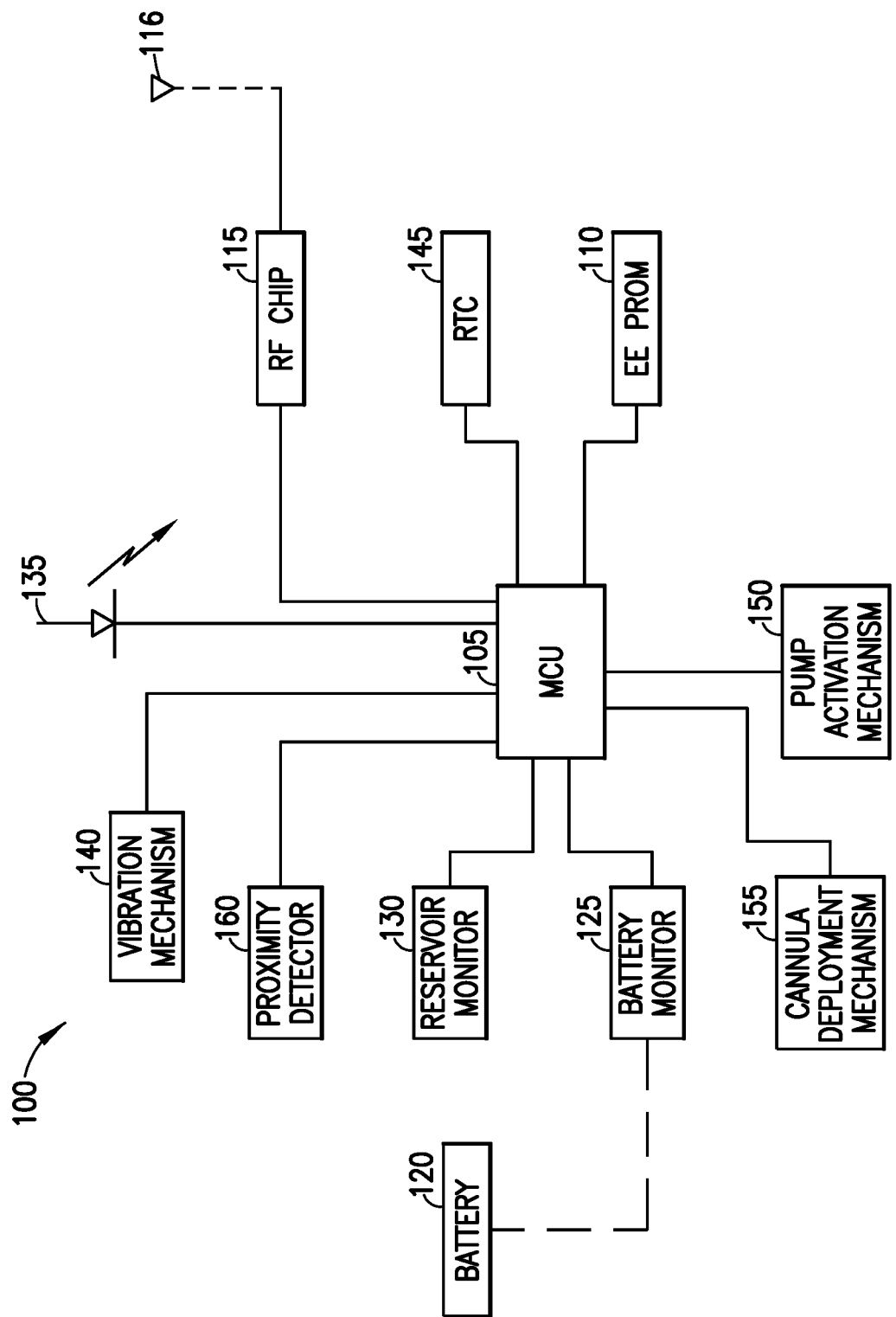
FIG. 1 depicts an illustrative embodiment of the components of an On-Body Medical Device (OBMD) of the present invention.
Figure 2:
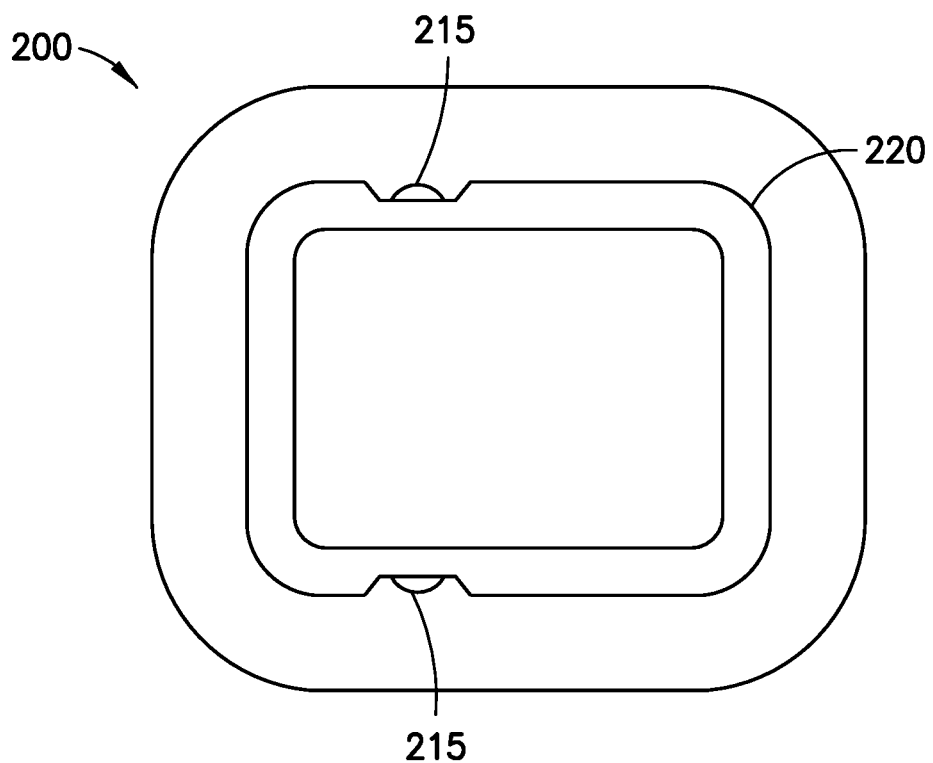
FIG. 2 depicts a top view of an illustrative embodiment of an OBMD of the present invention.
Figure 3:
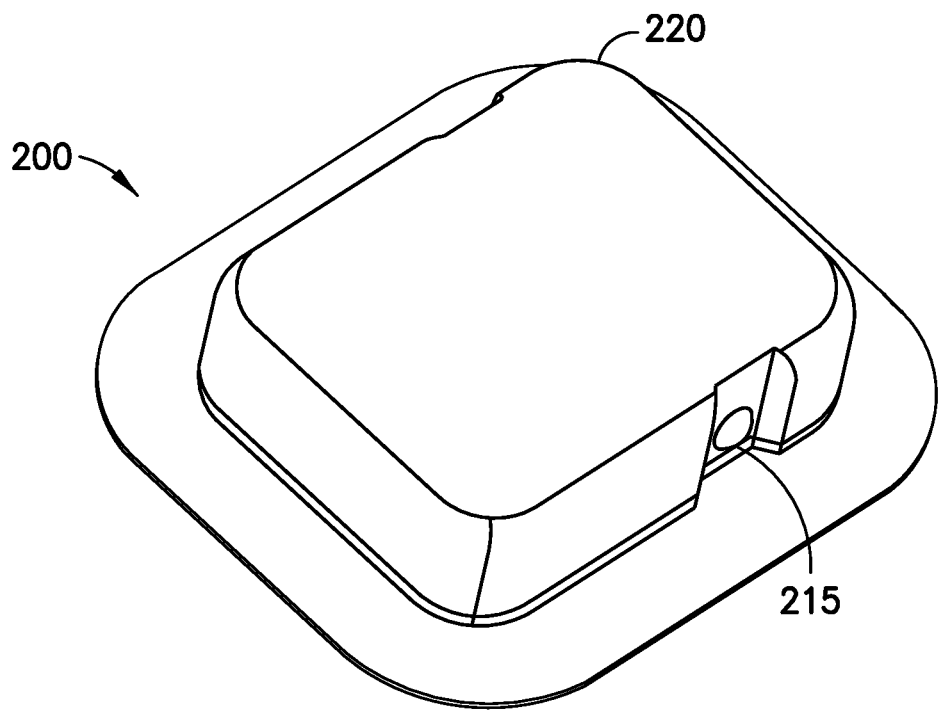
FIG. 3 depicts a perspective view of an illustrative embodiment of an OBMD of the present invention.
Figure 4:
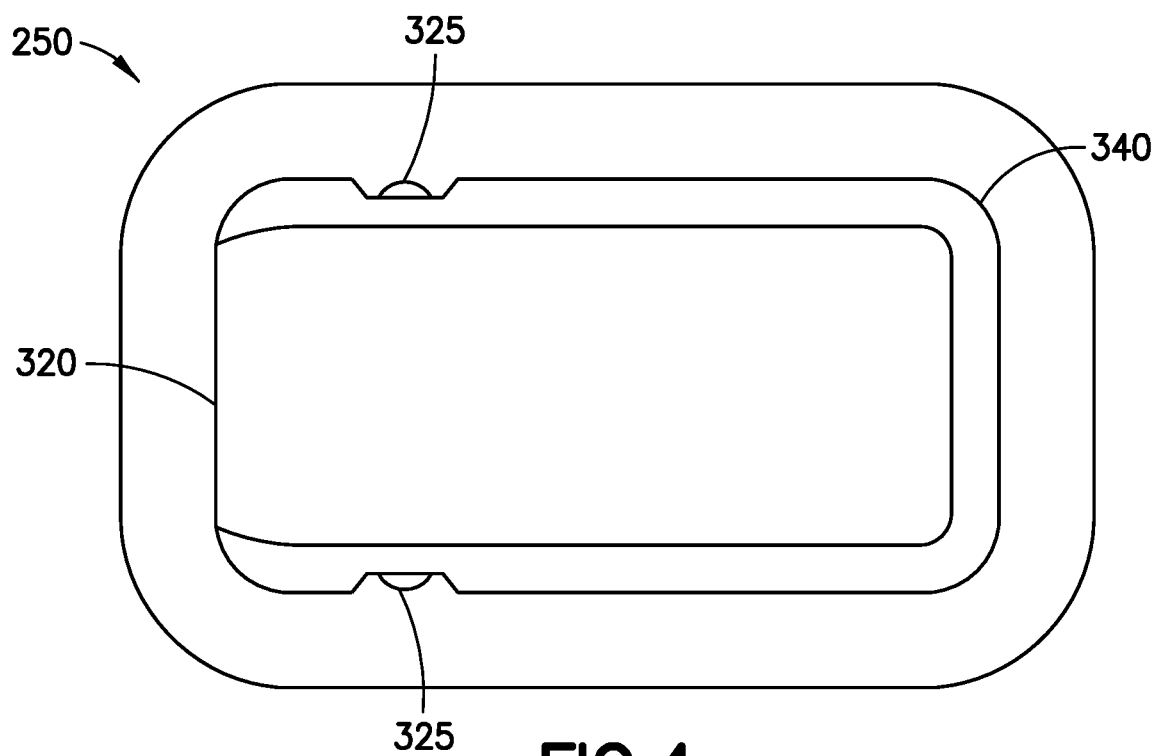
FIG. 4 depicts a top view of an illustrative embodiment of an OBMD of the present invention.
Figure 5:
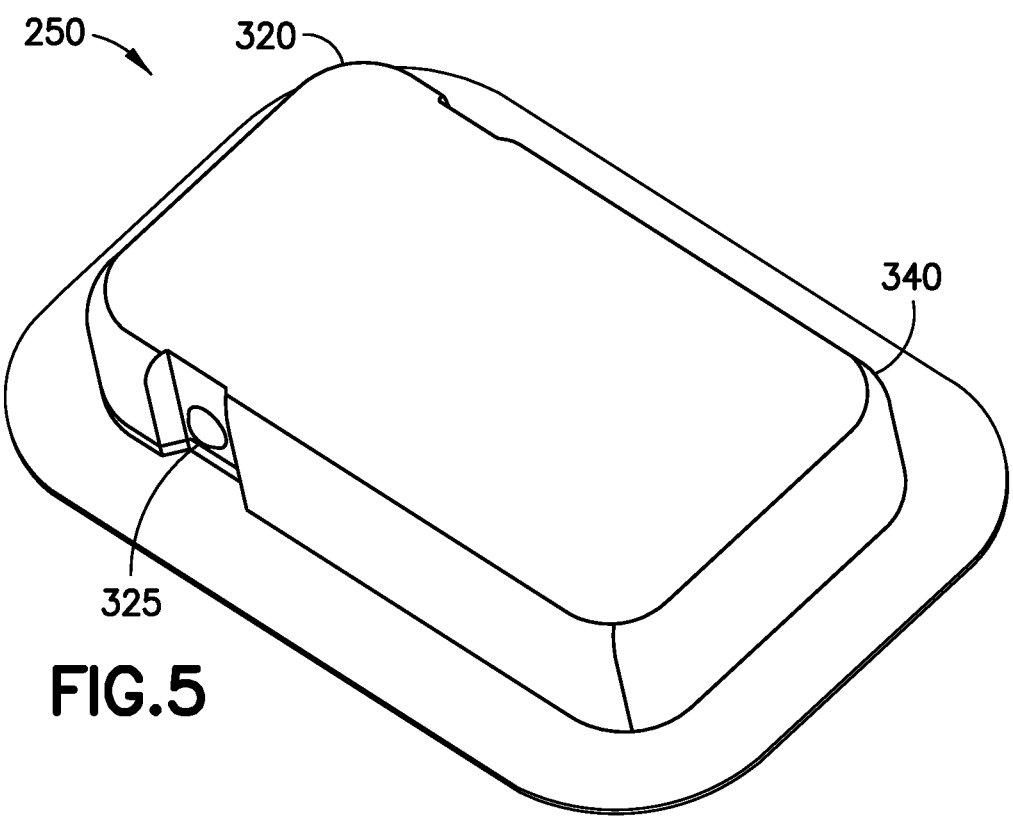
FIG. 5 depicts a perspective view of an illustrative embodiment of an OBMD of the present invention.

FIG. 1 depicts an illustrative embodiment of the components of a subcutaneous On-Body Medical Device (OBMD) 100 of the present invention. Referring to FIG. 1, an OBMD 100 generally includes a microprocessor control unit (MCU) 105, a memory (e.g., EEPROM) 110, an RF chip 115 and antenna 116, a battery 120, a battery monitor 125, a reservoir monitor 130, a light emitting diode (LED) 135, a vibration mechanism 140, a real time clock (RTC) 145, a pump activation mechanism 150, a cannula deployment mechanism 155, and a proximity detector 160.

The MCU 105 of the OMBD 100 is programmed to retrieve and execute instructions stored in the memory 110 to operate the OMBD 100 and activate the subcutaneous delivery of controlled amounts of insulin at set and variable rates to a user. Any number and type of processor(s) known to those of ordinary skill in the art such as an integrated circuit microprocessor, microcontroller, a digital signal processor (DSP), and/or a central processing unit (CPU), or other circuit or equivalent capable of interpreting instructions or performing logical actions on information, can be used in conjunction with illustrative embodiments of the present invention.

The memory 110 of the OBMD 100 stores instructions, medical device data, infusion programs and schedules, user log files, and any other data and parameters necessary for the OBMD 100 to operate as intended. The memory 110 operating in conjunction with the present invention may include any combination of different memory storage devices, such as hard drives, random access memory (RAM), read only memory (ROM), FLASH memory, or any other type of volatile and/or nonvolatile memory.

The RF chip 115 of the OBMD 100 is a two-way communication interface, including a receiver and a transmitter, for communicating with a remote user interface (UI) and another OBMD using radio frequency or other wireless communication standards and protocols. ZigBee, or any other WPAN protocol based on IEEE802.15.4, provides standardized, secure medical device communication in several widely available radio frequency allocations.

The battery 120 supplies power to the MCU 105. The battery is preferably integrated into the OBMD 100 or can be provided as a replaceable battery. A battery of any suitable type and size may be used.

The battery monitor 125 of the OMBD 100 determines whether the battery 120 is installed and monitors the level of voltage of the battery 120. The battery monitor 125 is adapted to report the presence or absence of an installed battery and compute or measure the amount of voltage stored in the installed battery. Additionally, if the battery 120 has a voltage capacity less than a predetermined threshold, the battery monitor 125 issues an alert to at least one of the OBMD 100 and a remote UI in the form of at least one of optical, acoustic, or tactile indications. Optical indication may be provided by a liquid crystal display (LCD), but may also be provided by other optical indicators such as a color light emitting diodes (LED) 135, organic light-emitting diodes (OLED), display text, display background colors, display backlight colors, and the like. Audible indication may be provided by a low power alarm, buzzer, or the like. Tactile indication may be provided by a vibratory mechanism 140, such as a piezo actuator.

The reservoir monitoring unit 130 is adapted to compute the volume of insulin stored by a reservoir of the OBMD 100. If the reservoir volume reaches a level less than a predetermined threshold, the reservoir monitor 125 issues an alert to at least one of the OBMD 100 and a remote UI in the form of at least one of an optical or an acoustic indication.

The RTC 145, which is a programmable clock for providing programs with real-time to track and control insulin delivery and initiate alarms at specific intervals, is utilized as part of the synchronization of the devices in illustrative embodiments of the present invention.

The pump activation mechanism 150 is adapted to deliver and meter insulin doses from the reservoir through a cannula that is inserted beneath the skin of a user when activated by the MCU 105.

The cannula deployment mechanism 155 is adapted to insert a cannula beneath the skin of a user when activated by instructions from a remote UI or, in the absence of a remote UI, instructions from another OMBD.

The proximity detector 160 is provided to extend product shelf-life and improve patient data security of RF-controlled devices having factory-installed, non-accessible primary-cell batteries. The proximity detector 160 communicates in lieu of the normal RF link for the purpose of initial synchronization and pairing with another medical device. By employing inductive coupling with relatively simple modulation, the proximity detector, drawing its operating power from the signal itself, remains ready to detect at all times without consuming any battery power at all. This improves responsiveness while extending shelf life of the OBMD 100. The proximity detector 160 is described more in detail in U.S. provisional patent application Ser. No. 61/576,309, filed on Dec. 15, 2011 and entitled "Method and Apparatus for Converting Continuous Glucose Monitoring Data to User-Friendly Video Format," the disclosure of which is incorporated by reference herein.

FIGS. 2-8 depict two illustrative embodiments of an OBMD of the present invention. In particular, FIGS. 2-8 depict a completely disposable patch pump 200 and a durable/disposable patch pump 250. Features of completely disposable patch pump 200 are shown on FIGS. 2-3 and include integral push-buttons 215 and an upper housing 220. Features of durable/disposable patch pump 250 are shown on FIGS. 4-8 and include a first upper housing 320, integral push-buttons 325, a second upper housing 340, an electrical connector 345 and O-ring seals 390. One or more push-buttons can be used to activate a manual bolus. Using more than one push-button may however reduce the chance of unintentional activation. For example, two opposing push buttons can be adapted to activate a manual bolus if pressed simultaneously.

Figure 9:
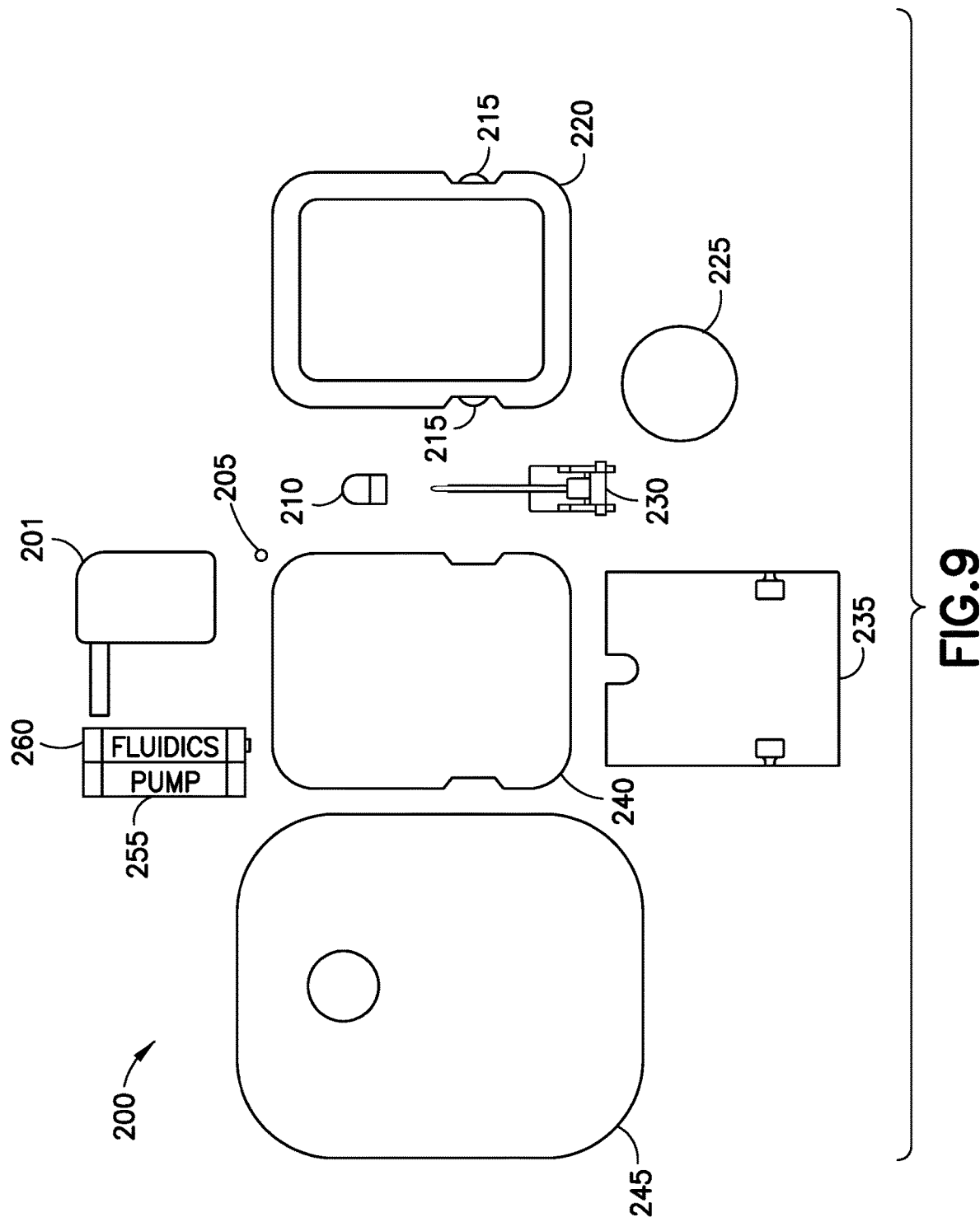
FIG. 9 depicts an exploded view of the mechanical components a completely disposable patch pump of an illustrative embodiment of the present invention.

FIG. 9 depicts an illustrative assembly embodiment of the completely disposable patch pump 200. The completely disposable patch pump includes a reservoir 201, a reservoir septum 205, a guide 210, integral push-buttons 215, an upper housing 220, a battery 225, a catheter deployment assembly 230, a printed circuit board assembly (PCBA) 235, a lower housing 240, a pressure sensitive adhesive 245, a pump engine 255, and a fluidic assembly 260. It should be understood that throughout this description the exemplary embodiments are described in connection with the use of a catheter. However, this is merely exemplary and those of ordinary skill in the art will readily appreciate that a rigid needle or any other suitable replacement may be used in the place of a catheter. Moreover, the term cannula is used to generically refer to catheters, needles, and the like. The completely disposable patch pump 200 is disposed of after a single use by a user. An antenna may be part of a PCBA or a separate component electrically connected to the PCBA.

Figure 10:
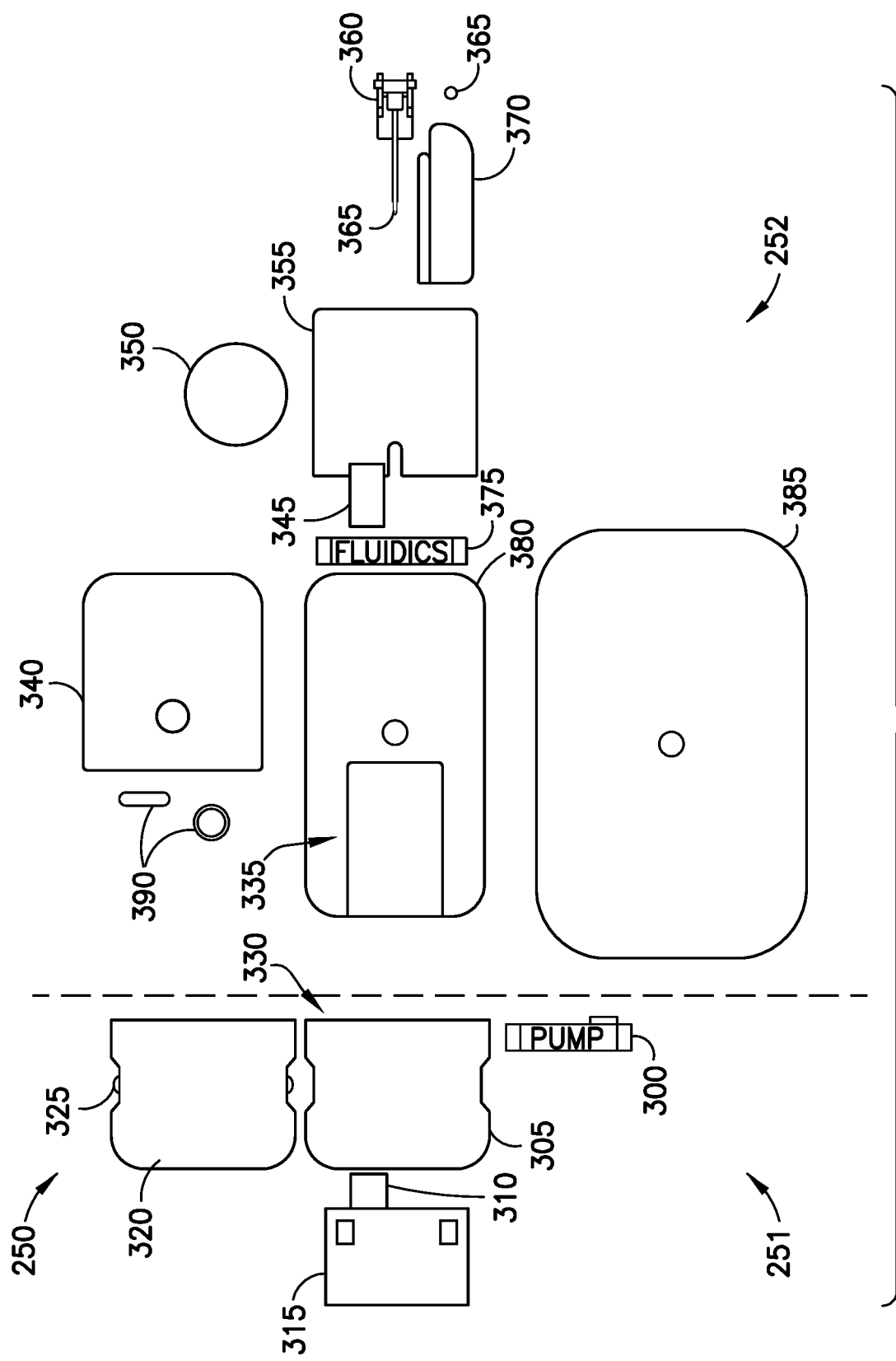
FIG. 10 depicts an exploded view of the mechanical components a durable/disposable patch pump of an illustrative embodiment of the present invention.

FIG. 10 depicts an illustrative assembly embodiment of the durable/disposable patch pump 250. The durable/disposable patch pump 250 includes a durable assembly 251 including a pump engine 300, a first lower housing 305, connector traces 310, a PCBA 315, a first upper housing 320, integral push-buttons 325, and a dovetail feature 330. The durable/disposable patch pump 250 also includes a disposable assembly 252 including a dovetail feature 335, a second upper housing 340, a connector 345, a battery 350, a PCBA 355, a catheter deployment assembly 360, a reservoir septum 365, a reservoir 370, a fluidic assembly 375, a second lower housing 380, a Pressure-Sensitive Adhesive (PSA) 385, and O-ring seals 390. An antenna may be part of a PCBA or a separate component electrically connected to the PCBA. Dovetail feature 330, or any other coupler known in the art, can be used to couple the durable assembly and the disposable assembly.

The durable and disposable assemblies 251, 252 of the durable/disposable patch pump 250 are connected via the channels of the dovetail feature 330, 335 and the connector 345 prior to application to the skin of a user. The disposable assembly 252 of the patch pump 250 is disposed of after a single exhaustive use by a user. However, the durable assembly 251 of the patch pump 250 is reusable when connected to another non-empty disposable assembly.

Figure 11:
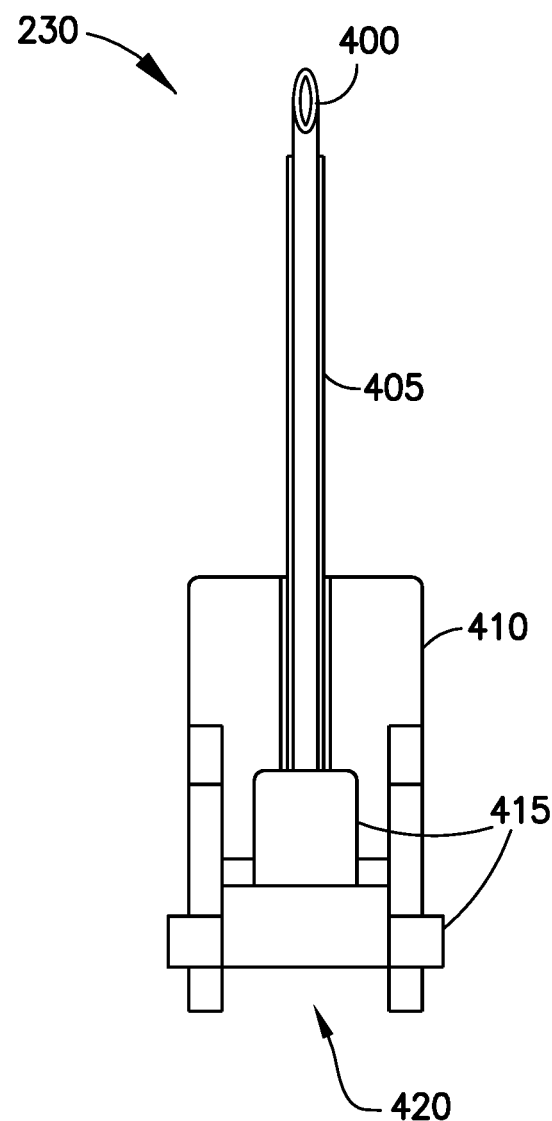
FIG. 11 depicts an illustrative embodiment of a catheter deployment assembly of the present invention.

FIG. 11 depicts an illustrative embodiment of the catheter deployment assembly 230, 360 for embodiments of the patch pumps 200 and 250 adapted to insert a catheter beneath the skin of a user when activated by instructions from a remote UI or, in the absence of a remote UI, instructions from another OMBD. The catheter deployment assembly 230, 360 includes an introducer needle 400, a catheter 405, a deployment carriage 410, a deployment spring (not shown), a retraction carriage 415, a retraction spring (not shown), and a tubing port 420.

Figure 12:
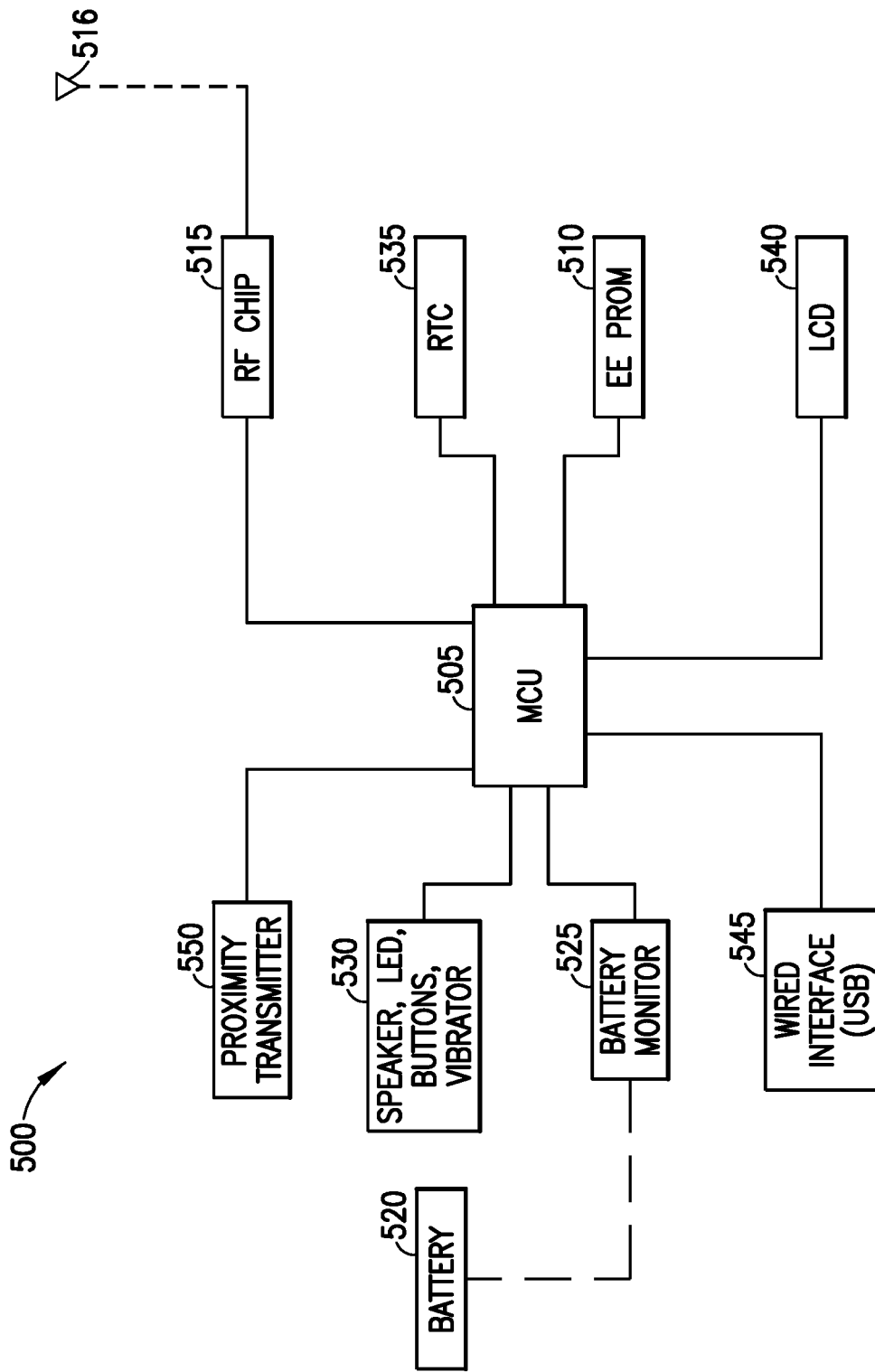
FIG. 12 depicts an illustrative embodiment of the components of a user interface (UI) of the present invention.

An illustrative embodiment of the components of a remote UI, such as a graphical user interface (GUI), personal digital assistant (PDA), or key fob of the present invention is illustrated in FIG. 12. Referring to FIG. 12, a remote UI 500 generally includes a microprocessor control unit (MCU) 505, a memory (e.g., EEPROM) 510, a RF chip 515 and antenna 516, a battery 520, a battery monitor 525, a speaker, LED (not shown), vibrator 530, a real time clock (RTC) 535, a LCD 540, a wired interface (USB) 545, and a proximity transmitter 550.

The MCU 505 of the remote UI 500 is programmed to retrieve and execute instructions stored in the memory 510 to operate the remote UI 500. Any number and type of processor(s) known to those of ordinary skill in the art such as an integrated circuit microprocessor, microcontroller, a digital signal processor (DSP), and/or a central processing unit (CPU), or other circuit or equivalent capable of interpreting instructions or performing logical actions on information, can be used in conjunction with illustrative embodiments of the present invention.

The memory 510 of the remote UI 500 stores instructions, medical device data, infusion programs and schedules, user log files, and any other data and parameters necessary for the remote UI 500 to operate as intended. The memory 510 operating in conjunction with the present invention may include any combination of different memory storage devices, such as hard drives, random access memory (RAM), read only memory (ROM), FLASH memory, or any other type of volatile and/or nonvolatile memory.

The RF chip 515 of the remote UI 500 is a two-way communication interface, including a receiver and a transmitter, for communicating with another remote UI and at least one OBMD 100 using radio frequency or other wireless communication standards and protocols.

The battery 520 supplies power to the MCU 505. A battery of any suitable type and size may be used.

The battery monitor 525 of the remote UI 500 determines whether the battery 520 is installed and monitors the level of voltage of the battery 520. If the battery 520 has a voltage capacity less than a predetermined threshold, the battery monitor 525 issues an alert to the remote UI 500 in the form of at least one of an optical or an acoustic indication. Optical indication may be provided by a liquid crystal display (LCD) 540, but may also be provided by other optical indicators such as a color light emitting diodes (LED) 530, organic light-emitting diodes (OLED), display text, display background colors, display backlight colors, and the like. Audible indication may be provided through a speaker 530 by a low power alarm, buzzer, or the like. Tactile indication may be provided by a vibratory mechanism 530, such as a piezo actuator.

The RTC 535, which is a programmable clock for providing programs with real-time to track and control insulin delivery and initiate alarms at specific intervals, is utilized as part of the synchronization of the devices in illustrative embodiments of the present invention.

The wired interface 545, such as a universal serial bus (USB) is provided for connection, communication and power supply between electronic devices.

The proximity transmitter 550 is provided to extend product shelf-life and improve patient data security of RF-controlled devices having factory-installed, non-accessible primary-cell batteries as addressed above.

Figure 13:
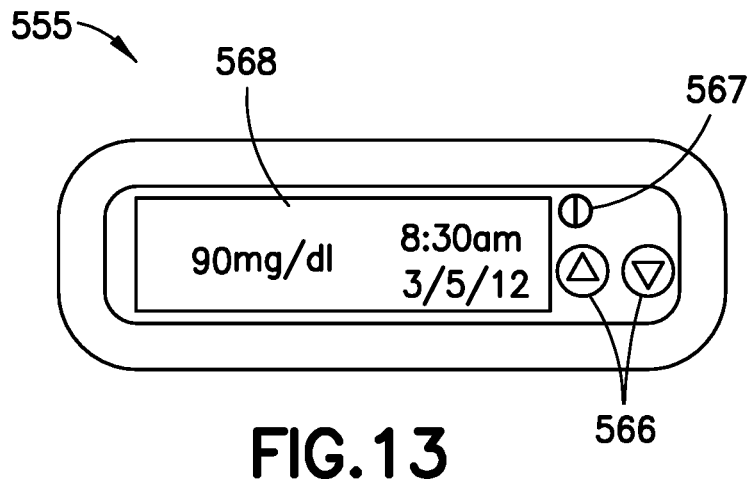
FIG. 13 depicts an illustrative embodiment of a fully-functioning GUI.
Figure 14:
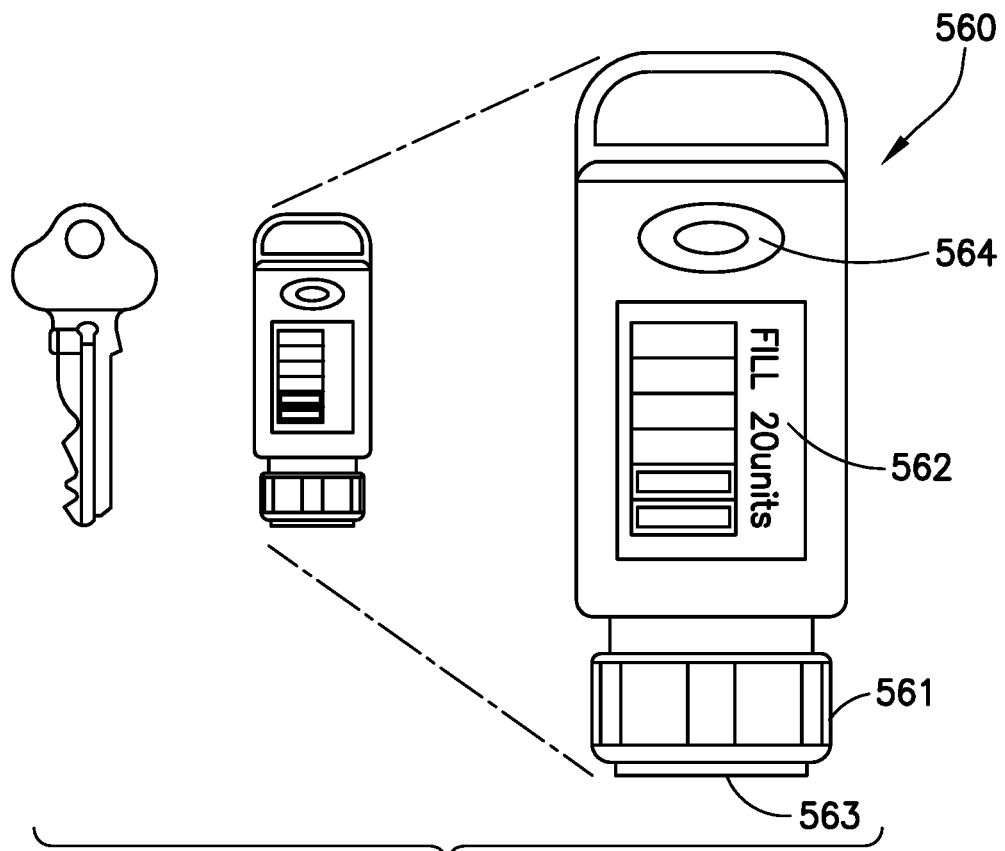
FIG. 14 depicts an illustrative embodiment of a minimally-functioning key fob.

FIGS. 13-14 depict two illustrative embodiments of a remote UI 500. Generally, UIs can be powered by primary cells, which would need to be replaced by the user periodically over the life of the UI. The UI can also be powered by secondary cells, also referred to as rechargeable cells. The life of secondary cells can be typically rated by the number of charge/discharge cycles, and these cells can last for a number of years.

FIG. 13 depicts an illustrative embodiment of a fully-functioning GUI 555. The fully-functioning GUI 555 has all available features necessary to control and administer the fluid delivery system of the present invention including the ability to communicate wirelessly with a health care network, either directly through the cellular network or indirectly through a PC or smartphone attached to the GUI using USB or Bluetooth, Bluetooth LE, ZigBee, or a custom communication protocol. Fully-functioning GUI 555 includes "up" and "down" buttons 566 to control the fluid delivery system, button 567 and display 568.

FIG. 14 depicts an illustrative embodiment of a minimally-functioning key fob 560. The primary purpose of the key fob 560 is to enable discrete bolus control and provide alarms when the user is in public. The key fob 560 mimics an insulin pen known to those of ordinary skill in the art. For example, the user can turn an end dial 561, visualize the dose on display 562, and depress the button 563 on the end similarly to depressing a button on an insulin pen. End dial 561 can instead be any dose setting device adapted to set a bolus dose. The design of the key fob 560 is also similar to the user interface portion of an insulin pen. For example, the key fob 560 has a body cross section, a dial for adjustment, a size graphics on the LCD screen, and a resistance to turning in the dial similar to those on an insulin pen. The overall length of the key fob 560 is similar to that of a house key. The key fob 560 includes a safety feature, e.g., a secondary push-button 564 or other button combined with a timer function to enable bolus infusions at predetermined intervals, and an additional safety feature to limit the maximum bolus delivered during a specific period of time. An illustrative key fob can be used to set and deliver a bolus. For example, a key fob can provide discrete bolus delivery functions when a user is in public. While embodiments of the minimally-functioning key fob described herein include bolus functions only, those of ordinary skill in the art will readily appreciate that the minimally functioning key fob could include the ability to adjust a basal rate in addition to setting a bolus dose.

For example, insulin doses are typically administered at a basal rate and in a bolus dose. Basal insulin is delivered continuously over period of time, and strives to keep one's blood glucose levels in a consistent range between meals and overnight. Some insulin pumps are capable of programming the basal rate of insulin to vary according to the different times of the day and night. Bolus doses are typically administered when the user takes a meal, and generally provide a single additional insulin injection to balance the carbohydrates consumed. Some conventional insulin pumps enable the user to program the volume of the bolus dose in accordance with the size or type of the meal consumed. Conventional insulin pumps also enable a user to take in a correctional or supplemental bolus of insulin to compensate for a low blood glucose level at the time the user is calculating a meal bolus.

An illustrative embodiment of a system for on-body fluid delivery can include a primary patch pump adapted to attach a first infusion cannula to a user, the primary patch pump further adapted to perform a plurality of primary patch pump functions, and a secondary patch pump adapted to attach a second infusion cannula to a user, the secondary patch pump further adapted to perform a plurality of secondary patch pump functions substantially similar to the plurality of primary patch pump functions if an error condition associated with the primary patch pump is determined.

In an illustrative embodiments of a system for on-body fluid delivery, the plurality of primary patch pump functions can include at least one of pairing with a primary user interface, being filled with a medicament and primed, deploying a catheter, initiating a bolus dose or basal rate, entering a primary patch pump SLEEP mode, entering a primary patch pump WAKE mode at predetermined primary patch pump WAKE time intervals, and entering a primary patch pump SNIFF mode for up to a predetermined primary patch pump SNIFF time.

In an illustrative embodiments of a system for on-body fluid delivery, a power level associated with a primary or secondary patch pump SLEEP mode can be lower than a power level associated with a primary or secondary patch pump WAKE mode.

In an illustrative embodiments of a system for on-body fluid delivery, the primary user interface can include a primary user interface real-time clock, and the primary patch pump can include a primary patch pump real-time clock. At least one of a SLEEP cycle, a WAKE cycle and a SNIFF cycle of the primary user interface can be synchronized with at least one of a SLEEP cycle, a WAKE cycle and a SNIFF cycle of a primary patch pump to save energy, using the primary user interface real-time clock and the primary patch pump real-time clock. Synchronization can be performed using a real-time clock.

In an illustrative embodiments of a system for on-body fluid delivery, the primary patch pump can be communicatively couplable to the secondary patch pump.

In an illustrative embodiments of a system for on-body fluid delivery, the primary patch pump can include one of a completely disposable patch pump and a durable/disposable patch pump. The completely disposable patch pump can include a reservoir to contain medicament, at least one integral push-button to activate a bolus dose, a catheter deployment assembly to deploy a catheter, a pump engine to infuse medicament from the reservoir through the deployed catheter, a printed circuit board assembly to control operations of at least one of the catheter deployment assembly and the pump engine, and an adhesive to attach the system to skin. The integral push-buttons can include two push-buttons to activate a bolus dose if both push-buttons are depressed simultaneously.

In an illustrative embodiments of a system for on-body fluid delivery, the durable/disposable patch pump can include a durable assembly and a disposable assembly, wherein the durable assembly includes a pump engine to infuse medicament from the reservoir, at least one integral push-button to activate a bolus dose, and a coupler feature to couple the durable assembly to the disposable assembly, and wherein the disposable assembly includes: a coupler feature to couple the disposable assembly to the durable assembly, a connector to electrically connect the disposable assembly to the durable assembly, a catheter deployment assembly to deploy a catheter, a reservoir to contain medicament, and an adhesive to attach the system to skin, and wherein at least one of the durable assembly and the disposable assembly includes a printed circuit board assembly to control operations of at least one of the pump engine and the catheter deployment assembly. The integral push-buttons can include two push-buttons to activate a bolus dose if both push-buttons are depressed simultaneously.

In an illustrative embodiments of a system for on-body fluid delivery, at least one of a primary user interface and a secondary user interface couplable to one or more patch pumps can include one of a fully-functioning graphical user interface and a minimally-functioning key fob. At least one of the primary user interface and the secondary user interface can include a timer function enabling bolus infusions at predetermined intervals. The minimally-functioning key fob can include a dose setting device, such as a turnable dial, adapted to set a bolus dose, and at least one depressible button adapted to initiate a bolus dose.

In an illustrative embodiments of a system for on-body fluid delivery, a primary user interface can be communicatively couplable to at least one of the primary patch pump and the secondary patch pump. The primary user interface can be communicatively couplable to a network link. A secondary user interface communicatively can be couplable to at least one of the primary patch pump and the secondary patch pump.

Illustrative embodiments for systems and methods of on-body fluid delivery of the present invention are depicted in FIGS. 15-21.

Figure 15:
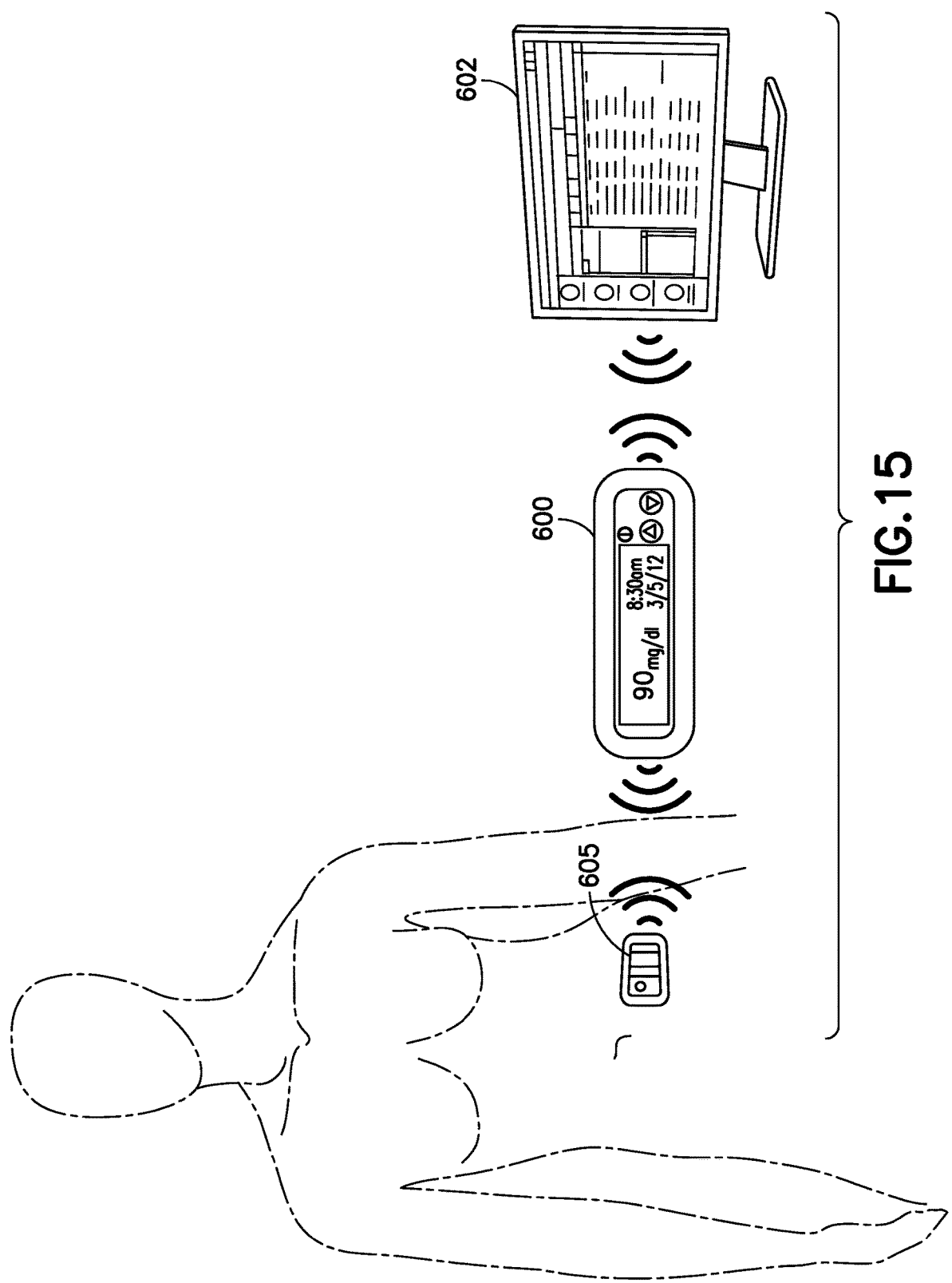
FIG. 15 depicts an illustrative embodiment of a wireless system for on-body fluid delivery in accordance with illustrative embodiments of the present invention.

FIG. 15 depicts an illustrative embodiment of a system for on-body fluid delivery in accordance with illustrative embodiments of the present invention, including a primary patch pump 605, a primary UI 600 and a network link 602. Primary patch pump 605 can include, for example, a wearable medical device patch pump glucose sensor. Primary UI 600 can include, for example, a graphical user interface, a personal data assistant or a cell phone application. Network link 602 can include, for example, a network link of personal computer, a network link of a mobile device, a network link of a cellular device, an internet link, and a gateway to a network such as a medical network.

Figure 16:
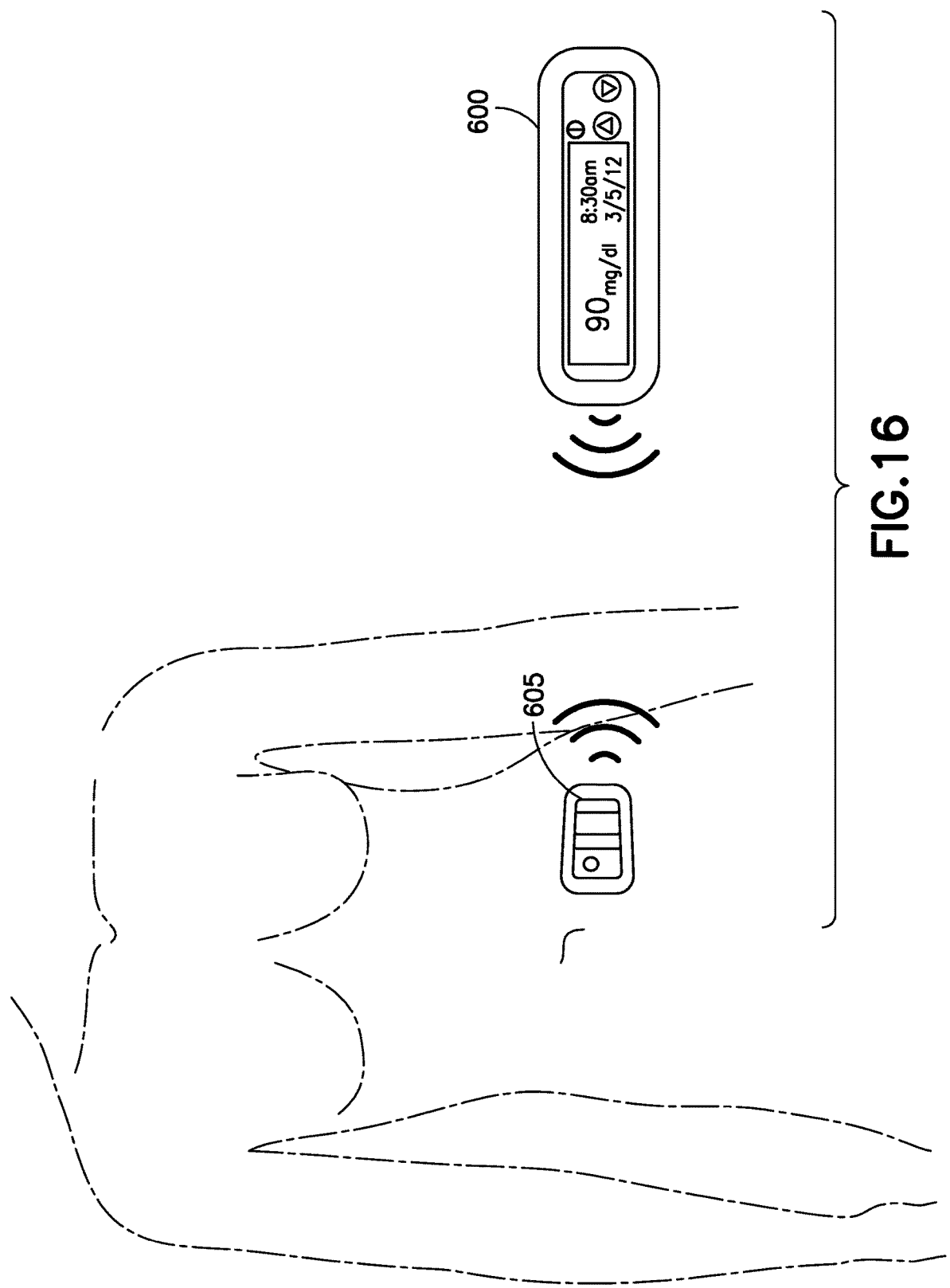
FIG. 16 depicts an illustrative embodiment of a wireless system for on-body fluid delivery between a primary UI and a primary patch pump.

FIG. 16 depicts an illustrative embodiment of a system for on-body fluid delivery between a primary UI 600 and a primary patch pump 605.

Figure 17:
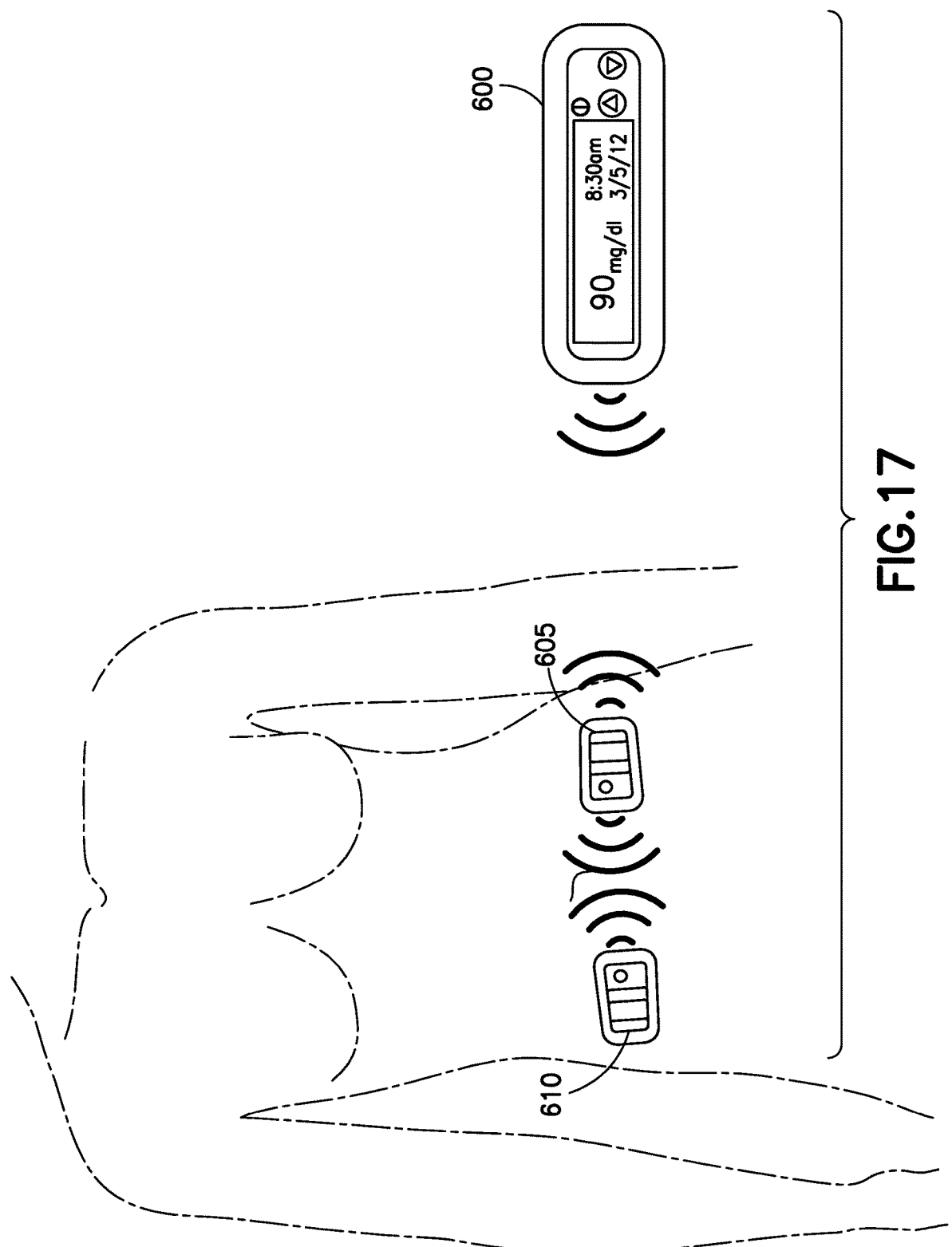
FIG. 17 depicts an illustrative embodiment of a wireless system for on-body fluid delivery between a combination of a primary UI, a primary patch pump, and a secondary patch pump.

FIG. 17 depicts an illustrative embodiment of a wireless system for on-body fluid delivery between a combination of a primary UI 600, a primary patch pump 605, and a secondary patch pump 610.

Figure 18:
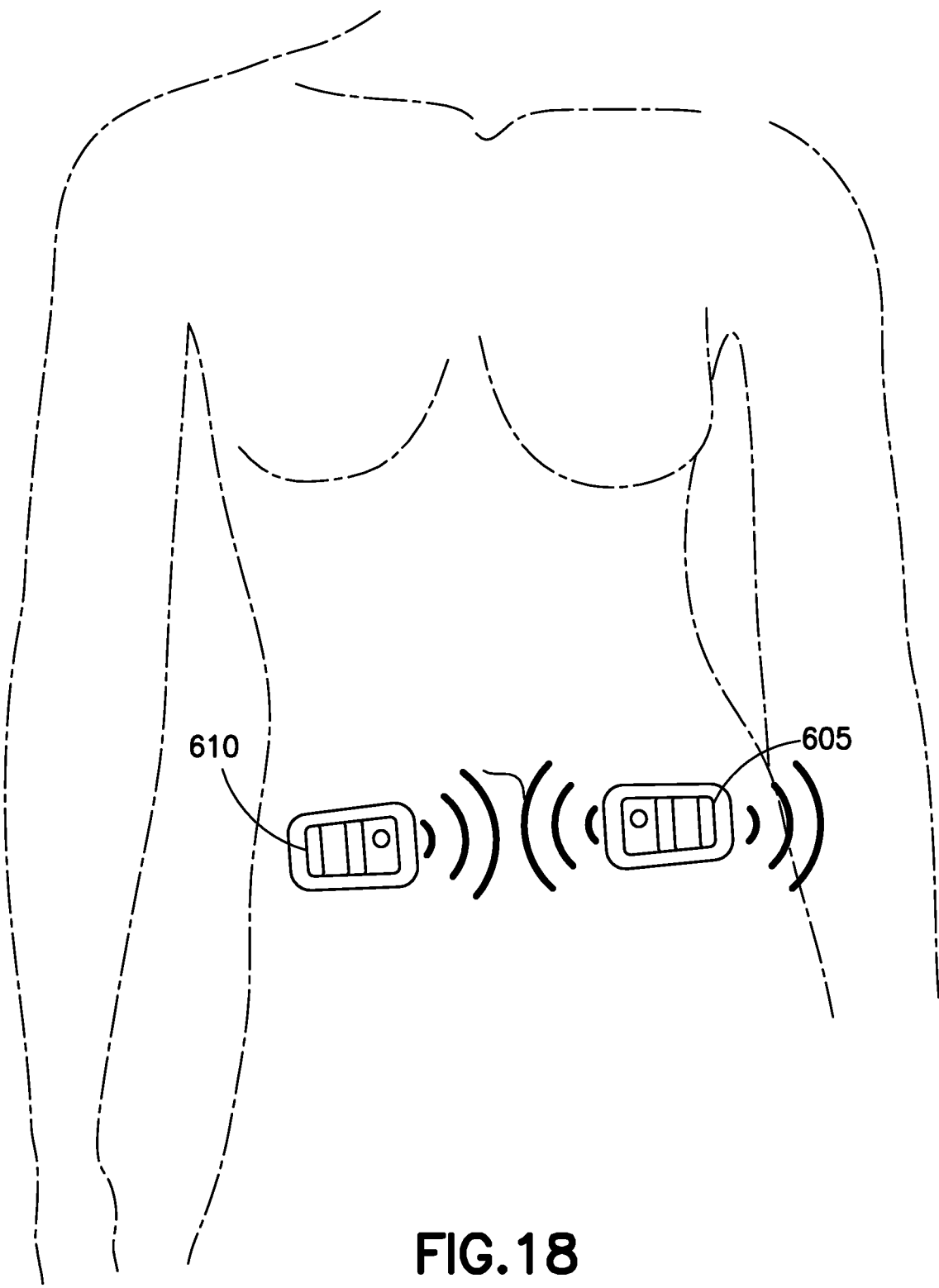
FIG. 18 depicts an illustrative embodiment of a wireless system for on-body fluid delivery between a primary patch pump and a secondary patch pump.

FIG. 18 depicts an illustrative embodiment of a wireless system for on-body fluid delivery between a primary patch pump 605 and a secondary patch pump 610.

Figure 19:
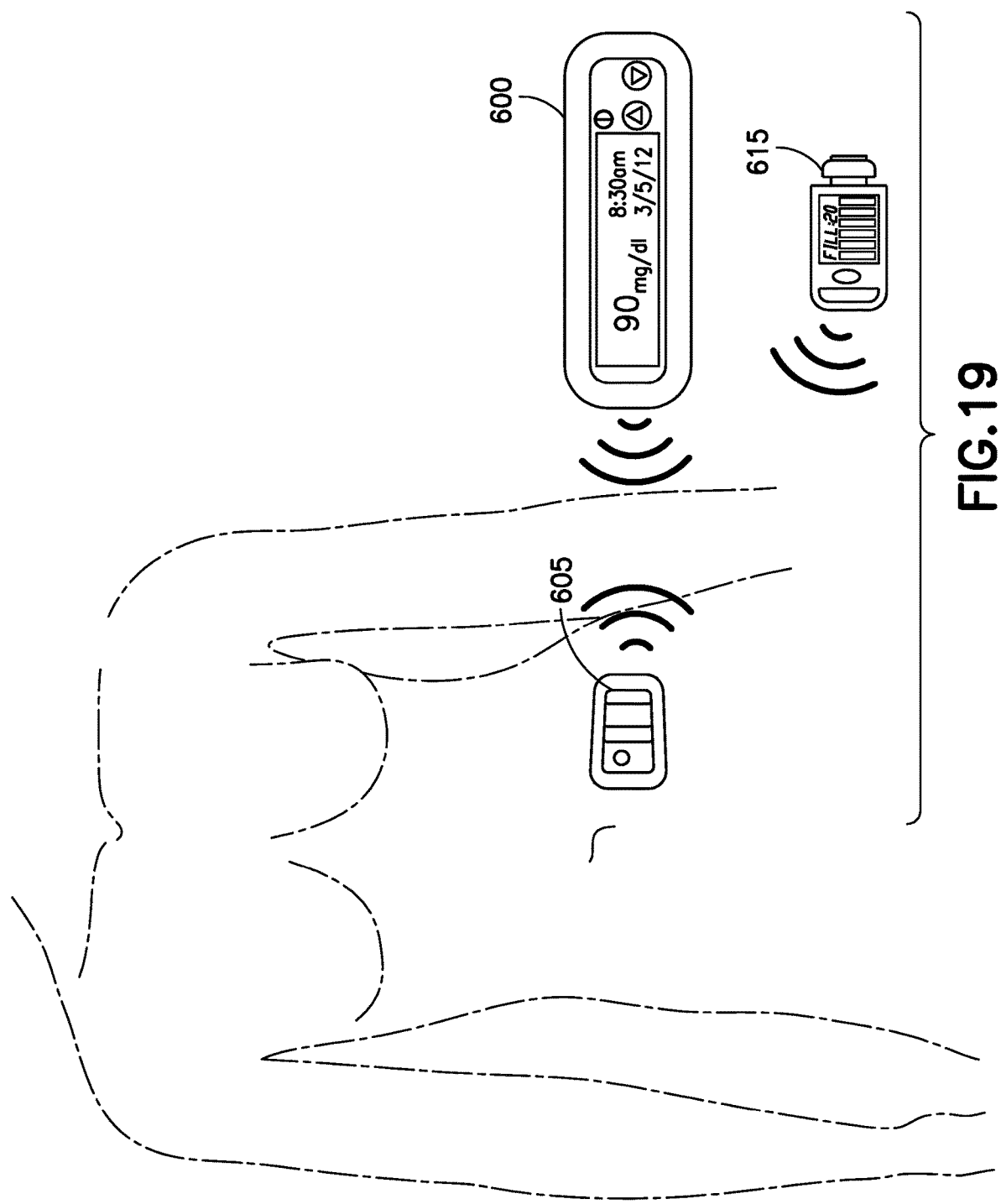
FIG. 19 depicts an illustrative embodiment of a wireless system for on-body fluid delivery between a combination of a primary UI, a secondary UI, and a primary patch pump.

FIG. 19 depicts another illustrative embodiment of a wireless system for on-body fluid delivery between a combination of a primary UI 600, a secondary UI 615, and a primary patch pump 605.

Figure 20:
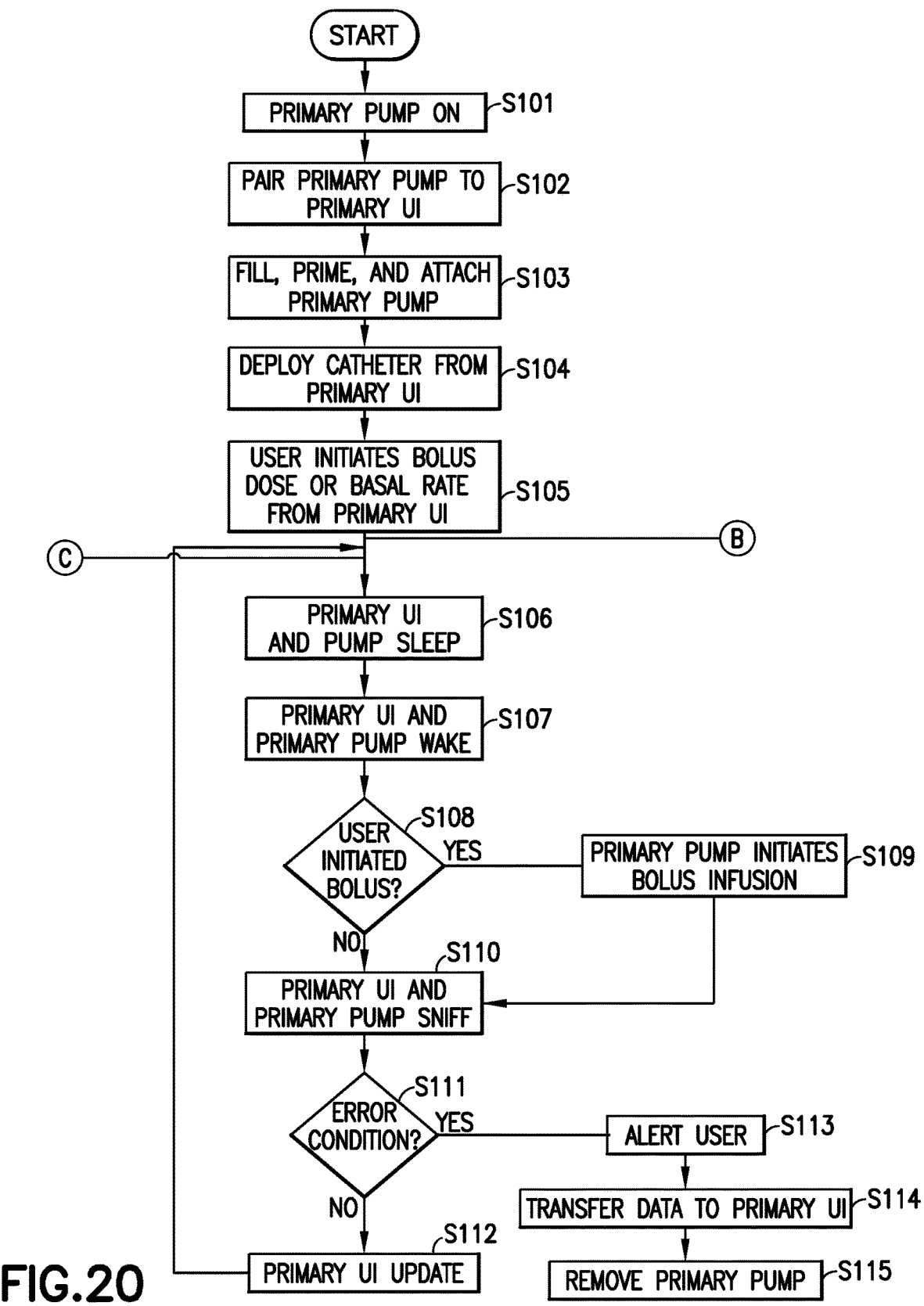
FIG. 20 depicts a flow chart illustrating an illustrative wireless method of on-body fluid delivery between a combination of a primary UI and a primary patch pump.

FIG. 20 depicts a flow chart illustrating an illustrative method of on-body fluid delivery between a combination of a primary UI and a primary patch pump. Referring to FIG. 20, a primary patch pump 605 is turned ON in step S101. The primary patch pump 605 is paired to the primary UI 600 in step S102. The pairing and the unique identifier for the pairing are assigned to the devices to enable secure, synchronized, encrypted wireless communication and minimize or eliminate cross-talk with other systems within the broadcast range.

The user then proceeds to fill the primary patch pump's reservoir with insulin, prime the primary patch pump 605 from the primary UI 600, and attach the primary patch pump 605 to the user's skin surface in step S103. The user can now deploy the catheter of the primary patch pump 605 from the primary UI 600 in step S104 to deliver incremental basal infusion. In step S105, the user initiates a bolus dose or basal rate. For example if the user initiates a basal rate of 2 units/hr from the primary UI 600, the primary UI 600 instructs the primary patch pump 605 to infuse a basal rate of approximately 0.5 units every 15 minutes.

In step S106, primary UI 600 and primary patch pump 605 go to "SLEEP". The primary UI 600 and primary patch pump 605 "WAKE" approximately once per minute as shown in step S107. If upon "waking", the primary patch pump 605 detects the primary UI 600 in active mode, then the primary patch pump 605 temporarily enters an "improved-response-time" mode with somewhat increased power consumption. In step S108, the primary patch pump 605 communicates with the primary UI 600 to determine whether the user initiated a mealtime bolus during the last cycle. If so, the primary patch pump 605 will begin a bolus infusion of 1 unit/min, for example, as shown in step S109.

The primary patch pump 605 will "SNIFF" for up to one second or a predetermined time in step S110 and check for an error condition in step S111. An error condition can comprise of one or more of conditions such as catheter occlusion, low reservoir, end of reservoir, battery depleted, battery failure, catheter deployment, entrapped air, and leakage.

The "SLEEP," "WAKE," and "SNIFF" cycles are constantly ongoing at regular intervals in the background and are transparent to the user. If the user engages the primary UI 600 to adjust basal rate or set a bolus delivery, the primary UI 600 immediately wakes, but after adjustment or setting remains synchronized to the "SLEEP," "WAKE," and "SNIFF" cycles of the primary patch pump 605.

If no error condition exists, the primary patch pump 605 exchanges relevant data with the primary UI 600 such as transferring an infusion profile update to the primary UI 600, receiving infusion commands from the primary UI 600, such as bolus dose requirements or basal rate adjustment, delivering the bolus dose and making any adjustments to the basal rate, and transmitting confirmation of delivery and/or adjustment at step S112 and steps S106 to S112 are repeated until an error condition occurs. Relevant data can comprise data indicative of at least one an infusion profile update, an infusion command, a bolus dose, a bolus dose requirement, a basal rate, a basal rate adjustment, a confirmation of delivery, an error state or condition, and a confirmation of adjustment.

If an error condition exists in step S113, the primary patch pump 605 will alert the user in step S113 and communicates relevant data to the primary UI in step S114. The primary patch pump 605 is now ready to be removed in step S115.

Figure 21:
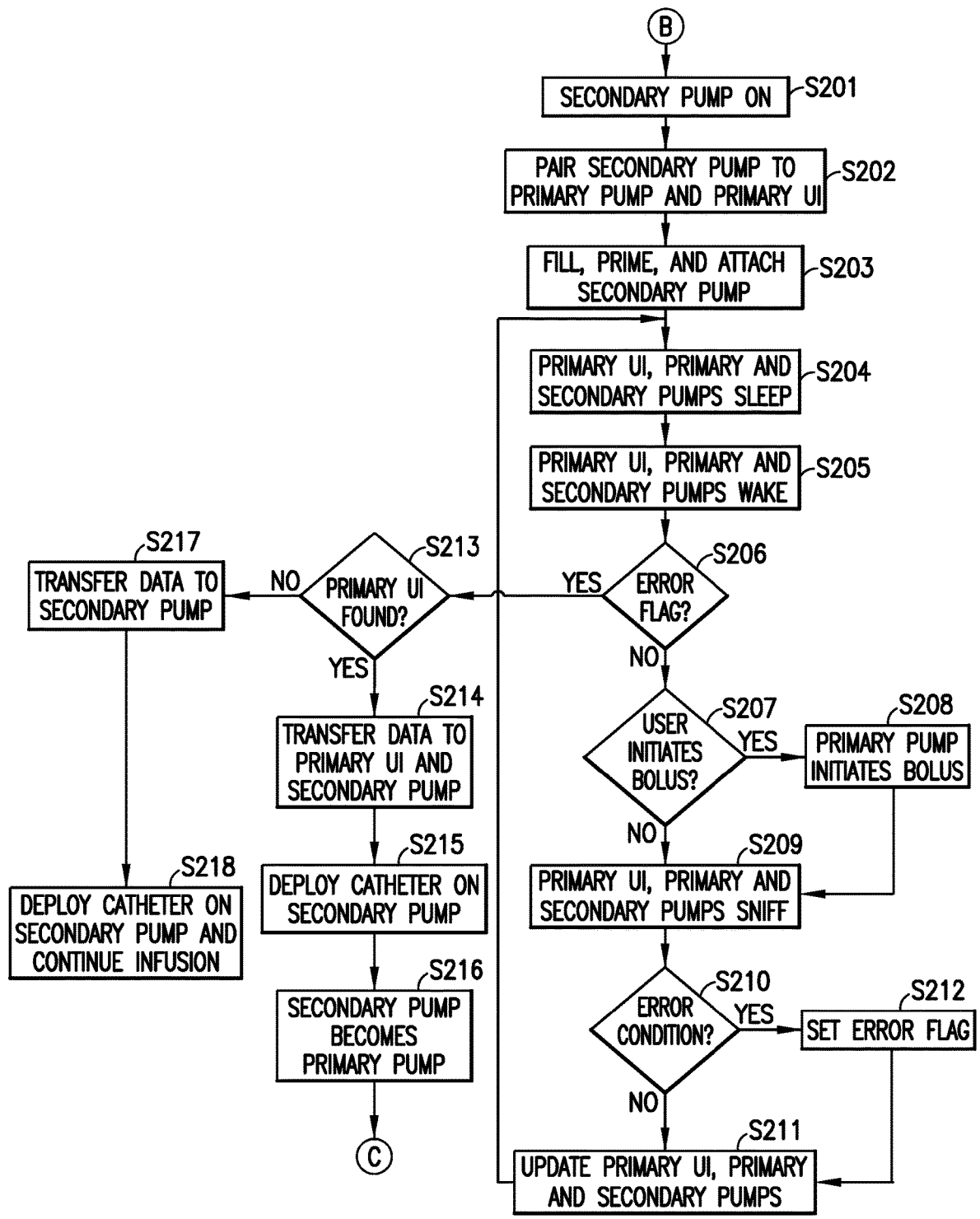
FIG. 21 depicts a flow chart illustrating an illustrative wireless method of on-body fluid delivery between a combination of a primary UI, a primary patch pump, and a secondary patch pump.

FIG. 21 depicts a flow chart illustrating an illustrative wireless method of on-body fluid delivery between a combination of a primary UI, a primary patch pump, and a secondary patch pump. Referring to FIG. 21, with the primary patch pump 605 already deployed and delivering incremental basal infusion, a user preemptively turns ON the secondary patch pump 610 on the last cyclical day of the primary patch pump 605 in step S201.

The secondary patch pump 610 is paired to both the primary UI 600 and the primary patch pump 605 in step S202. The user then proceeds to fill the secondary patch pump's reservoir with insulin, prime the secondary patch pump 610 from the primary UI 600, and attach the secondary patch pump 610 to the user's skin surface in step S203.

At this juncture, both the primary patch pump 605 and the secondary patch pump 610 are simultaneously attached to the user's skin surface. However, the catheter of secondary patch pump 610 is not yet deployed at this time. The primary UI 600, the primary patch pump 605 and the secondary patch pump 610 "SLEEP," "WAKE," and "SNIFF" together in steps S204, S205, and S209.

During this time, the user may initiate a bolus dose as shown in step S207 that will trigger the primary patch pump 605 to initiate a bolus does as shown in step S208 during the next "WAKE" cycle of step S205.

The secondary patch pump 610 will remain awake until the bolus dose has been delivered. If there is insufficient insulin in the reservoir of the primary patch pump 605, then the secondary patch pump 610 will activate, deploy its catheter, and complete the bolus delivery. The "SLEEP," "WAKE," and "SNIFF" cycles are constantly ongoing at regular intervals in the background and are transparent to the user. If the user engages the primary UI 600 to adjust basal rate or set a bolus delivery, the primary UI 600 immediately wakes, but after setting or adjustment remains synchronized to the "SLEEP," "WAKE," and "SNIFF" cycles of the primary and secondary patch pumps 605, 610.

If no error condition is detected in step S210, then the primary UI 600, the primary patch pump 605, and the secondary patch pump 610 are updated with the latest relevant data at step S211 and steps S204-S211 are repeated until an error condition occurs and an error flag is detected at step S206. If an error condition occurs at step S210, an error flag is set at step S212, the primary UI 600, the primary patch pump 605, and the secondary patch pump 610 are updated with the latest relevant data at step S211 and steps S204-S211 are repeated until an error condition occurs.

Accordingly, at the next "WAKE" step S207, the error flag is present at step S206, thus initiating a transfer from the primary patch pump 605 to the secondary patch pump 610. If the primary UI 600 is detected in step S213, then the primary patch pump 605 communicates relevant data to the primary UI 600 and the secondary patch pump 610. The primary UI 600 then deploys the catheter on the secondary patch pump 610 at step S215. The secondary patch pump 610 takes over the role of a primary patch pump at step S216. Preferably, another preemptive patch pump can be attached to the user and can take over the role of a secondary patch pump.

If, however, no primary UI 600 is detected at step S213, then the primary patch pump 605 communicates relevant data to the secondary patch pump 610 at step S217. Accordingly, the catheter is deployed on the secondary patch pump 610 and infusion continues via the secondary patch pump 610 at step S218.

A "SLEEP" mode can be associated with a power consumption level lower than to power consumption level associated with a "WAKE" mode. Since the "SLEEP" duration can be minutes long, the background on the LCD screen 540 on the UIs 600, 615 can change colors to correspond to "dose requested" (yellow), to "dose delivered" (green), and red for a failure condition or alarm to eliminate confusion for the user as to whether the dose has been communicated and delivered. When these states do not need to be communicated to the user, there is no color to the background of the LCD screens of the UIs 600,615 and the LCD 540 can turn off, as is the case for "sleep" mode. Audible and tactile signals can also be provided for the three states described above, which are distinctly different for each condition.

In another illustrative embodiment of the present invention depicted in FIG. 19, an additional secondary UI 615 may be activated. In this embodiment, a secondary UI 615, such as a key fob 560, may be used as an additional tool to wirelessly enable discrete bolus control and provide alarms when the user is in public. In the presence of both a primary UI 600 and a secondary UI 615, the primary UI 600 is dominant.

A situation might arise where the patch pumps 605, 610 wake and do not recognize two UIs 600, 615 (e.g. during travel, when primary UI 600 is in a user's luggage or car trunk and cannot be recognized by the patch pumps 605, 610), but the user only has the ability to use the secondary UI 615 to provide bolus. In this situation, secondary UI 615 can be enabled in the same way in which a patch pump was brought out of "shelf" mode and "paired" with the master UI, that is, by bringing secondary UI 615 in proximity with the patch pumps 605, 610. This process is described more in detail in U.S. provisional patent application Ser. No. 61/576, 309, filed on Dec. 15, 2011 and entitled "Method and Apparatus for Converting Continuous Glucose Monitoring Data to User-Friendly Video Format," the disclosure of which is incorporated by reference herein. In illustrative embodiments, when two UIs wake and recognize each other following this event, relevant data is preferably transferred from UI2 to UI1, and UI1 preferably assumes the dominant role.

Alternatively, when the patch pumps 605, 610 wake and recognize only secondary UI 615, a duration can be established (e.g., 30 seconds) to continue to "sniff" for primary UI 600, after which time secondary UI 615 can provide a command to the patch pumps 605, 610. The two UIs 600, 615, however, should not both be enabled to provide commands to the patch pump at the same time.

FIGS. 22A-24B depict illustrative embodiments of fourteen different states 1-14 and operations for activated medical devices of the fluid delivery system of the present invention. The system operation associated with each different combination of a primary patch pump (Patch Pump 1 or PP1), a secondary patch pump (Patch Pump 2 or PP2), a primary UI (User Interface 1 or UI1), and a secondary UI (User Interface 2 or UI2) is disclosed in the state diagram table in FIGS. 22A-24B. FIGS. 22A-24B also depict illustrative embodiments where communications failure can occur (e.g., states where patch pump 1 is not recognized by the other devices in the system when all the devices wake) and how embodiments of the present invention continue to provide safe, uninterrupted therapy to a user.

In state 1, an illustrative system includes PP1. Illustrative system Operations can proceed as follows. PP1 was initially paired to UI1, which synchronized the "sleep", "wake", "sniff" cycle of both devices. In the absence of UI1, PP1 will wake, conduct self-diagnostics, sniff for the UI1, and then return to sleep. PP1 continues to provide basal infusion at the rate previously transmitted from the UI. Bolus delivery can be initiated manually by the user via the push-buttons on PP1.

In state 2, an illustrative system includes PP1 and UI1. Illustrative system Operations can proceed as follows. PP1 was initially paired to UI1, which synchronized the "sleep", "wake", "sniff" cycle of both devices. PP1 will wake, conduct self-diagnostics, sniff, recognize UI1, transfer the infusion profile update which occurred since the previous update was transmitted, receive infusion commands, e.g. bolus dose requirement or basal rate adjustment, deliver the bolus dose and make any adjustments to the basal rate, transmit confirmation of delivery and/or adjustment, and then return to sleep.

In state 3, an illustrative system includes PP1, UI1 and UI2. Illustrative system Operations can proceed as follows. PP1 was initially paired to UI1, and UI2 was also paired to UI1, which synchronized the "sleep", "wake", "sniff" cycle of all three devices. PP1 will wake, conduct self-diagnostics, sniff, recognize both UI1 and UI2, PP1 will transfer to both UIs the infusion profile update which occurred since the previous update was transmitted. However, in the presence of both UIs, PP1 will only receive infusion commands from UI1, e.g. bolus dose requirement or basal rate adjustment. Following the delivery of the bolus dose and any required adjustments to the basal rate, PP1 will transmit confirmation of delivery and/or adjustment, and then return to sleep.

In state 4, an illustrative system includes PP1 and UI2. Illustrative system Operations can proceed as follows. PP1 was initially paired to UI1, and UI2 was also paired to UI1, which synchronized the "sleep", "wake", "sniff" cycle of all three devices. PP1 will wake, conduct self-diagnostics, sniff, recognize only UI2. In the absence of UI1, PP1 will transfer to UI2 the infusion profile update which occurred since the previous update was transmitted. Since UI2 can only provide a single infusion command, i.e. a bolus dose requirement, PP1 will receive the bolus dose command from UI2, and following the delivery, PP1 will transmit confirmation of delivery to UI2, and then return to sleep. Either UI2 or PP1 will update UI1, the next time UI1 is recognized as the devices in the system continue to wake, sniff, and sleep.

In state 5, an illustrative system includes PP1 and PP2. Illustrative system Operations can proceed as follows. PP1 was initially paired to UI1, and PP2 was also paired separately to UI1, which synchronized the "sleep", "wake", "sniff" cycle of all three devices. In the absence of UI1, PP1 will wake, conduct self-diagnostics, sniff for UI1 and any other devices to which PP1 has been paired, transfer to PP2 the infusion profile update which occurred since the previous update was transmitted, and then return to sleep. Bolus delivery can be provided manually by the user. If a manual bolus command is provided by the user to PP1, then upon waking both PP1 and PP2 will remain awake until the complete bolus dose has been delivered. If there is insufficient insulin remaining in the reservoir of PP1, PP1 will communicate the remaining requirement to PP2, and the basal deliver rate. PP2 will then deploy the infusion catheter, deliver the remainder of the bolus dose, and return to sleep. After receiving confirmation from PP2, PP1 will disable all infusion capability and return to the synchronized sleep, wake, sniff cycle. PP2 will now operate as PP1 in state 1, and continue to provide basal infusion, and manually actuated, incremental bolus dosing. If upon waking PP2 recognizes UI1, then PP2 will update UI1, and then PP2 and UI1 will operate as PP1 and UI1 in state 2. The catheter in PP1 can be automatically retracted and the adhesive can be automatically dissolved from a command provided by UI1, or PP1 can be manually removed from the skin surface of the user.

In state 6, an illustrative system includes PP1, PP2 and UI1. Illustrative system Operations can proceed as follows. PP1 was initially paired to UI1, and PP2 was also paired separately to UI1, which synchronized the "sleep", "wake", "sniff" cycle of all three devices. Together PP1 and PP2 will wake, conduct self-diagnostics, sniff, and recognize UI1. PP1 will transfer to UI1 the infusion profile update which occurred since the previous update was transmitted. UI1 will transfer to PP2 the infusion profile update which occurred since the previous update was transmitted. PP1 will receive infusion commands from UI1. These may include adjustments to the basal rate or bolus infusion commands. Following the setting and/or delivery of the bolus dose or adjusted basal rate, PP1 will transmit confirmation of delivery and/or adjustment to UI1, and UI1 will in turn transmit the update to PP2, and then all three devices will return to sleep. If there is insufficient insulin remaining in the reservoir of PP1 to complete the required bolus delivery or if PP1 is exhausted during basal delivery, PP1 will communicate the remaining requirement to UI1. After receiving confirmation from UI1, PP1 will disable all infusion capability and return to the synchronized sleep, wake, sniff cycle. UI1 will then transfer the remaining bolus requirements and/or basal rate to PP2. PP2 will then deploy the infusion catheter, take over basal rate infusion and/or deliver the remainder of the bolus dose, transmit confirmation of the remaining bolus dose, and return to sleep. PP2 will now operate as PP1 in state 2.

In state 7, an illustrative system includes PP1, PP2, UI1 and UI2. Illustrative system Operations can proceed as follows. PP1 was initially paired to UI1, PP2 was paired separately to UI1, and UI2 was also paired to UI1, which synchronized the "sleep", "wake", "sniff" cycle of all four devices. Together PP1 and PP2 will wake, conduct self-diagnostics, sniff, and recognize both UI1 and UI2. PP1 will transfer to both UIs the infusion profile update which occurred since the previous update was transmitted. UI1 will transfer to PP2 the infusion profile update which occurred since the previous update was transmitted. In the presence of both UIs, PP1 will receive infusion commands from UI1. These may include adjustments to the basal rate or bolus infusion commands. Following the setting and/or delivery of the bolus dose and any required adjustments to the basal rate, PP1 will transmit confirmation of delivery and/or adjustment to both UI1 and UI2, and UI1 will in turn transmit the update to PP2, and then all four devices will return to sleep. If there is insufficient insulin remaining in the reservoir of PP1 to complete the required bolus delivery or if PP1 is exhausted during basal delivery, PP1 will communicate the remaining requirement to UI1. After receiving confirmation from UI1, PP1 will disable all infusion capability and return to the synchronized sleep, wake, sniff cycle. UI1 will then transfer the remaining bolus requirements and/or basal rate to PP2. PP2 will then deploy the infusion catheter, take over basal rate infusion and/or deliver the remainder of the bolus dose, transmit confirmation of the remaining bolus dose and resumption of basal delivery, and all four devices will return to sleep. PP2 will now operate as PP1 in state 3. The user can attach a new patch pump, which will take over the role of preemptive patch pump PP2.

In state 8, an illustrative system includes PP1, PP2 and UI2. Illustrative system Operations can proceed as follows. PP1 was initially paired to UI1, PP2 was paired separately and UI1, and UI2 was also paired to UI1, which synchronized the "sleep", "wake", "sniff" cycle of all four devices. Together PP1 and PP2 will wake, conduct self-diagnostics, sniff, and recognize only UI2. PP1 will transfer to UI2 the infusion profile update which occurred since the previous update was transmitted. UI2 will transfer to PP2 the infusion profile update which occurred since the previous update was transmitted. In the absence of UI1, PP1 will receive bolus infusion commands from UI2. These may include adjustments to the basal rate or bolus infusion commands. Following the setting and/or delivery of the bolus dose, PP1 will transmit confirmation of delivery and/or adjustment to UI2, and UI2 will in turn transmit the update to PP2, and then all three devices will return to sleep. If there is insufficient insulin remaining in the reservoir of PP1 to complete the required bolus delivery or if PP1 is exhausted during basal delivery, PP1 will communicate the remaining requirement to UI2. After receiving confirmation from UI2, PP1 will disable all infusion capability and return to the synchronized sleep, wake, sniff cycle. UI2 will then transfer the remaining basal rate and/or bolus dose requirement to PP2. PP2 will deploy the infusion catheter, take over basal rate infusion and/or deliver the remainder of the bolus dose, transmit confirmation of the bolus dose and resumption of basal delivery, and all three devices will return to sleep. PP2 will now operate as PP1 in state 4. If upon waking PP2 recognizes UI1, then PP2 and UI1 will operate as PP1 and both UIs in state 3, and either UI2 or PP2 will update UI1, the next time UI1 is recognized as the devices in the system continue to wake, sniff, and sleep.

In state 9, an illustrative system includes UI1. Illustrative system Operations can proceed as follows. If upon waking, UI1 does not recognize a PP, then an alarm is provided to the user.

In state 10, an illustrative system includes UI2. Illustrative system Operations can proceed as follows. If upon waking, UI2 does not recognize a PP, then an alarm is provided to the user.

In state 11, an illustrative system includes UI1 and UI2. Illustrative system Operations can proceed as follows. If upon waking, both UI1 and UI2 do not recognize a PP, then an alarm is provided to the user.

In state 12, an illustrative system includes PP2 and UI1. Illustrative system Operations can proceed as follows. PP1 was initially paired to UI1, and PP2 was also paired separately to UI1, which synchronized the "sleep", "wake" "sniff" cycle of all three devices. PP2 will wake, conduct self-diagnostics, sniff, and recognize only UI1. In the absence of PP1. UI1 will transfer to PP2 any user updates for bolus dose requirement, basal rate, or basal rate adjustment. PP2 will then deploy the infusion catheter, deliver the bolus dose, transmit confirmation of the bolus dose delivery and resumption of basal delivery, and return to sleep. PP2 will now operate as PP1 in state 2. UI1 will provide an alarm or any other visual, audio or tactile alert mechanism known in the art to alert the user that PP1 is no longer functioning properly and should~ be removed. UI1 will remain awake for two cycles sniffing for PP1, following which UI1 will resume the synchronized sleep, wake sniff cycle. (PP1 internal protocols will disable all infusion capability once a communication failure is detected.)

In state 13, an illustrative system includes PP2 and UI2. Illustrative system Operations can proceed as follows. PP1 was initially paired to UI1, PP2 was paired separately to UI1 and UI2 was also paired to UI1, which synchronized the "sleep", "wake", "sniff" cycle of all four devices. PP2 will wake, conduct self-diagnostics, sniff, and recognize only UI2, In the absence of PP1 and UI1, UI2 will transfer to PP2 any user updates for bolus dose requirement. PP2 will then deploy the infusion catheter, deliver the bolus dose, transmit confirmation of the bolus dose delivery and resumption of basal delivery, and return to sleep. PP2 will now operate as PP1 in state 3. UI2 will provide an alarm or any other visual, audio or tactile alert mechanism known in the art to alert the user that PP1 is no longer functioning properly and should be removed. UI2 will remain awake for two cycles sniffing for PP1, following which UI will resume the synchronized sleep, wake, snuff, cycle. (PP1 internal protocols will disable all infusion capability once a communication failure is detected.)

In state 14, an illustrative system includes PP2, UI1 and UI2. Illustrative system Operations can proceed as follows. PP1 was initially paired to UI1, PP2 was paired separately to UI1, and UI2 was also paired to UI1, which synchronized the "sleep", "wake", "sniff" cycle of all four devices. PP2 will wake, conduct self-diagnostics, sniff and recognize only UI1 and UI2. In the absence of PP1, UI1 will transfer to PP2 any user updates for bolus dose requirement or basal rate adjustment. PP2 will then deploy the infusion catheter, deliver the bolus dose, transmit confirmation of the bolus dose delivery and resumption of basal delivery, and return to sleep. PP2 will now operate as PP1 in state 2. UI1 will provide an alarm to alert the user that PP1 is no longer functioning properly and should be removed. UI1 will remain awake for two cycles sniffing for PP1, following which UI1 will resume the synchronized sleep, wake, sniff cycle. (PP1 internal protocol will disable all infusion capability once a communication failure is detected.)

As discussed above, the RTCs utilized in the medical devices of the fluid delivery system of the present invention can vary due to inherent limitations on accuracy and ambient conditions such as temperature and other factors. The maximum error in the current state of the art for RTCs is approximately 2 minutes per year, which equates to approximately one second over three days.

An embodiment of the present invention overcomes the inherent limitations on accuracy of electronic clocks utilized in medical devices with wireless communication, such as RTCs, by controlling protocol timing incrementally, using only short intervals.

According to an embodiment of the present invention, the fluid delivery system provides a one second window each time the medical devices "WAKE" to enable all the devices to recognize the active devices in the system. For example, therapeutic functions cannot be executed until all the devices in the system are awake.

In cases where drifting occurs the master device can re-synchronize all the devices in the system. For example, a primary user interface can re-synchronize itself with a secondary user interface, a primary patch pump, and/or a secondary patch pump. This operation is transparent to the user, and advantageously assists in synchronizing the sleep and wake cycles of the different devices to improve battery management and prolong battery life.

As described above, the user can initiate a bolus delivery from the UI while the OBMDs sleep, and upon waking the bolus will be delivered. Therefore, the user would not need to wait for the OBMDs to wake when the user is inputting a command into a remote UI.

In an illustrative method of on-body fluid delivery using a primary user interface communicatively couplable to a primary patch pump, the primary patch pump can include a first reservoir adapted to contain a first fluid, a first catheter, a first pump adapted to infuse the first fluid from the first reservoir through the first catheter, and a first microcontroller adapted to control operations of the first pump.

An illustrative method of on-body fluid delivery can include pairing the primary patch pump to the primary user interface. The primary patch pump can communicate with the primary user interface to determine whether user instructions have been received at the primary user interface. If it is determined that user instructions have been received at the primary user interface, machine instructions can be sent from the primary user interface to the primary patch pump according to the user instructions, and a bolus dose or basal rate can be initiated using the first microcontroller according to the machine instructions.

An illustrative method of on-body fluid delivery can further include checking by the primary patch pump for an error condition. If an error condition is detected by the primary patch pump, a user can be alerted via an alert mechanism and transferring relevant data from the primary patch pump to the primary user interface. If no error condition is detected by the primary patch pump, relevant data can be transferred from the primary patch pump to the primary user interface. The method can return to the step of the primary patch pump communicating with the primary user interface.

In an illustrative method of on-body fluid delivery, an error condition can include a condition indicative of at least one of a catheter occlusion, a low reservoir, an end of reservoir, a depleted battery, a battery failure, a catheter deployment, entrapped air and a leakage. Relevant data can include data indicative of at least one an infusion profile update, an infusion command, a bolus dose, a bolus dose requirement, a basal rate, a basal rate adjustment, a confirmation of delivery, an error state or condition, and a confirmation of adjustment.

In an illustrative method of on-body fluid delivery, the primary user interface can re-synchronize the primary user interface and the primary patch pump.

In an illustrative method of on-body fluid delivery, pairing the primary patch pump to the primary user interface can include assigning a first unique identifier to the primary user interface and a second unique identifier to the primary patch pump.

An illustrative method of on-body fluid delivery can further include entering a primary patch pump SNIFF mode for up to a predetermined primary patch pump SNIFF time to check for an error condition.

In an illustrative method of on-body fluid delivery, the primary patch pump can be attachable to skin. The first fluid can include insulin.

An illustrative method of on-body fluid delivery can further include entering a primary user interface SLEEP mode by the primary user interface, entering a primary patch pump SLEEP mode by the primary patch pump, entering a primary user interface WAKE mode by the primary user interface at predetermined primary user interface WAKE time intervals, and entering a primary patch pump WAKE mode by the primary patch pump at predetermined primary patch pump WAKE time intervals. A power level associated with the primary user interface SLEEP mode can be lower than a power level associated with a primary user interface WAKE mode, and a power level associated with the primary patch pump SLEEP mode can be lower than a power level associated with a primary patch pump WAKE mode.

In an illustrative method of on-body fluid delivery, if the primary patch pump detects the primary user interface, a primary patch pump IMPROVED-RESPONSE-TIME mode can be entered by the primary patch pump to communicate with the primary user interface to determine whether user instructions have been received at the primary user interface.

In an illustrative method of on-body fluid delivery, at least one of a SLEEP cycle, a WAKE cycle and a SNIFF cycle of the primary user interface can be synchronized with at least one of a SLEEP cycle, a WAKE cycle and a SNIFF cycle of the primary patch pump.

In an illustrative method of on-body fluid delivery, if the primary user interface is engaged for an adjustment of basal rate or a setting of bolus delivery, after the adjustment or setting at least one of a SLEEP cycle, a WAKE cycle and a SNIFF cycle of the primary user interface is synchronized with at least one of a SLEEP cycle, a WAKE cycle and a SNIFF cycle of the primary patch pump.

An illustrative method of on-body fluid delivery can further include using a secondary patch pump communicatively couplable to at least one of the primary patch pump and the primary user interface. The secondary patch pump can include a second reservoir adapted to contain a second fluid, a second catheter, a second pump adapted to infuse the second fluid from the second reservoir through the second catheter, and a second microcontroller adapted to control operations of the second pump.

An illustrative method of on-body fluid delivery can further include pairing the secondary patch pump to the primary user interface, and checking for an error flag. If no error flag is detected, the primary patch pump can communicate with the primary user interface to determine whether user instructions have been received at the primary user interface. If it is determined that user instructions have been received at the primary user interface, machine instructions can be sent from the primary user interface to the primary patch pump according to the user instructions, and a bolus dose or basal rate can be initiated using the first microcontroller according to the machine instructions.

An illustrative method of on-body fluid delivery can further include checking for an error condition. If an error condition is detected, an error flag can be set. If no error condition is detected, relevant data can be transferred from the primary patch pump to the primary user interface and the secondary patch pump. The method can return to the step of checking for an error flag.

In an illustrative method of on-body fluid delivery, an error condition can include a condition indicative of at least one of a catheter occlusion, a low reservoir, an end of reservoir, a depleted battery, a battery failure, a catheter deployment, entrapped air and a leakage. Relevant data can include data indicative of at least one an infusion profile update, an infusion command, a bolus dose, a bolus dose requirement, a basal rate, a basal rate adjustment, a confirmation of delivery, an error state or condition, and a confirmation of adjustment.

An illustrative method of on-body fluid delivery can further include entering a primary patch pump SNIFF mode for up to a predetermined primary patch pump SNIFF time to check for an error flag.

An illustrative method of on-body fluid delivery can further include continuing an infusion via the secondary patch pump if an error flag is detected.

An illustrative method of on-body fluid delivery can further include, if an error flag is detected, determining whether the primary user interface is communicatively coupled to the primary patch pump. If no primary user interface is determined to be communicatively coupled to the primary patch pump, transferring relevant data from the primary patch pump to the secondary patch pump, and continuing an infusion via the secondary patch pump. If a primary user interface is determined to be communicatively coupled to the primary patch pump, relevant data can be transferred from the primary patch pump to the secondary patch pump and to the primary user interface, the secondary pump can be set as the primary pump, and the method can return to the step of the primary patch pump communicating with the primary user interface. Another preemptive patch pump can be set as the secondary patch pump.

In an illustrative method of on-body fluid delivery, the primary patch pump can be attachable to skin. The primary user interface can re-synchronize the primary user interface and at least one of the primary patch pump and the secondary patch pump.

In an illustrative method of on-body fluid delivery, pairing the secondary patch pump to the primary user interface can include assigning a third unique identifier to the secondary patch pump. The second fluid can include insulin.

An illustrative method of on-body fluid delivery can further include entering a primary user interface SLEEP mode by the primary user interface, entering a primary patch pump SLEEP mode by the primary patch pump, entering a secondary patch pump SLEEP mode by the secondary patch pump, entering a primary user interface WAKE mode by the primary user interface at predetermined primary user interface WAKE time intervals, entering a primary patch pump WAKE mode by the primary patch pump at predetermined primary patch pump WAKE time intervals, and entering a secondary patch pump WAKE mode by the secondary patch pump at predetermined secondary patch pump WAKE time intervals.

In an illustrative method of on-body fluid delivery, if the primary user interface is engaged for an adjustment of basal rate or a setting of bolus delivery, after the adjustment or setting at least one of a SLEEP cycle, a WAKE cycle and a SNIFF cycle of the primary user interface can be synchronized with at least one of a SLEEP cycle, a WAKE cycle and a SNIFF cycle of the primary patch pump and with at least one of a SLEEP cycle, a WAKE cycle and a SNIFF cycle of the secondary patch pump to save energy.

In an illustrative method of on-body fluid delivery, at least one of a SLEEP cycle, a WAKE cycle and a SNIFF cycle of the primary user interface can be synchronized with at least one of a SLEEP cycle, a WAKE cycle and a SNIFF cycle of the primary patch pump and with at least one of a SLEEP cycle, a WAKE cycle and a SNIFF cycle of the secondary patch pump to save energy.

Additional embodiments of the present invention can overcome disadvantages such as the inconvenience and tissue damage caused by removing the adhesive backing 245, 385 of a patch pump from a user's skin surface as executed in step S115 of FIG. 20. Referring to FIGS. 25-30c, illustrative embodiments of the present invention leverage the power, circuitry and mechanization of a patch pump to control and release an adhesive solvent, such as siloxane, in order to minimize tissue damage and additional user steps needed to remove a patch pump device.

An illustrative embodiment of an adhesive removal apparatus can be adhere to skin with an adhesive pad having an adhesive. The adhesive removal apparatus can comprise at least one adhesive solvent reservoir in a base of a body of the device, the at least one adhesive solvent reservoir containing adhesive solvent. The adhesive solvent can be releasable from the at least one adhesive solvent reservoir to act on the adhesive and release the adhesive pad from skin upon the device receiving a release signal.

The adhesive solvent can be encapsulated in the at least one adhesive solvent reservoir. The adhesive solvent can flow through at least one hole in the base of the body of the device when the adhesive solvent is released. The adhesive solvent can be at least partially comprised of siloxane. The adhesive solvent can contact and dissolve the adhesive from the adhesive pad when the adhesive solvent is released. The adhesive solvent can wick to the adhesive pad and dissolve the adhesive from the adhesive pad.

Figure 25:
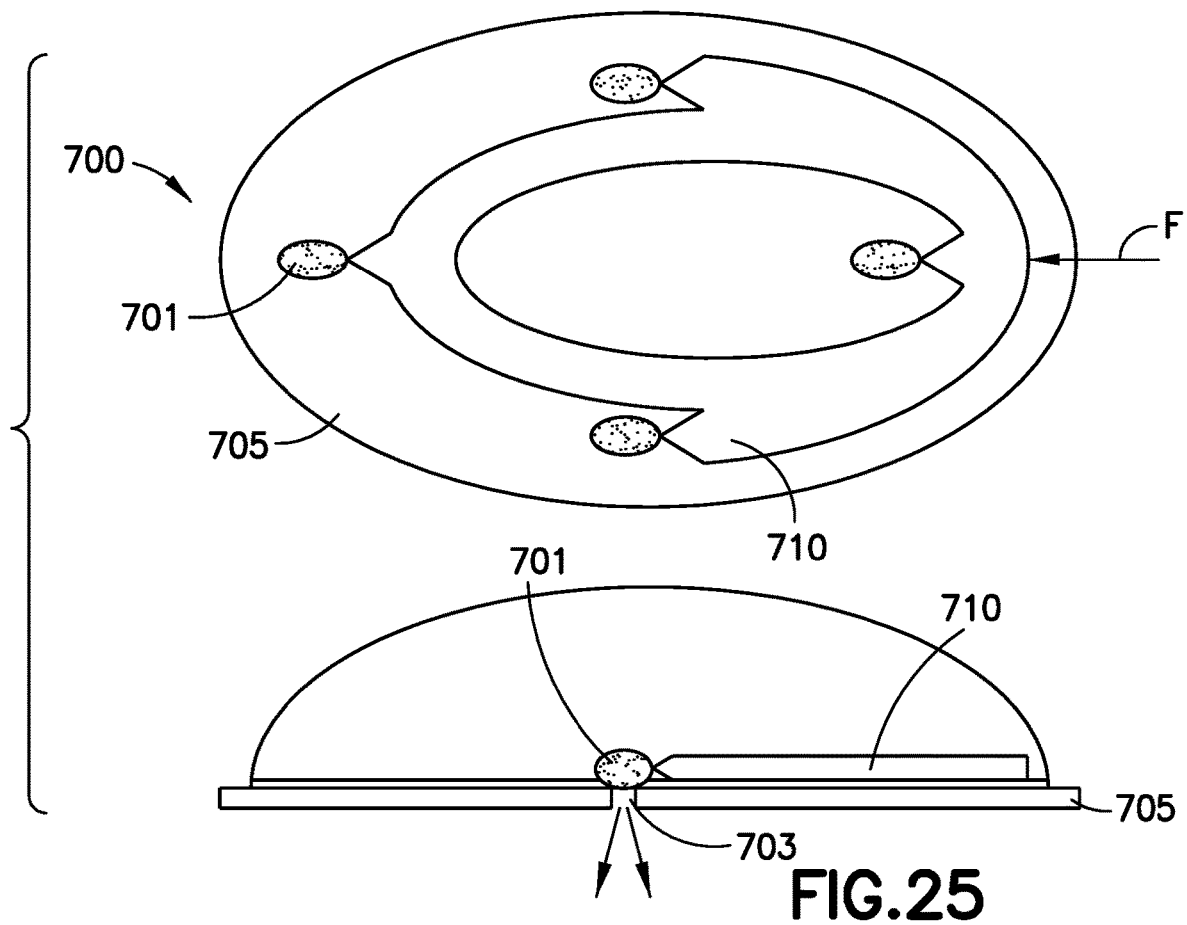
FIG. 25 depicts an illustrative embodiment of an adhesive removal apparatus of the present invention using multiple reservoir punctures.

FIG. 25 depicts an illustrative embodiment of an adhesive removal apparatus 700 using multiple reservoir punctures. Adhesive solvent is encapsulated in several adhesive solvent reservoirs 701 in the base of a body 705 of a device adapted to adhere to skin. A release signal can trigger a force supplied by a shape memory alloy (SMA) wire, a motor, or the like. A force F moves the puncture ring 710 forward, thus piercing the adhesive solvent reservoirs 701. Force F can be triggered locally or remotely. The adhesive solvent then flows through holes 703 in the bottom of the base of the device body 705, contacts and then releases the adhesive pad from the skin. For example, an adhesive solvent can wick through an adhesive as part of the adhesive dissolving process.

In an illustrative embodiment of an adhesive removal apparatus, a puncture ring can be movable to puncture the at least one adhesive solvent reservoir and release adhesive solvent. The puncture ring can be movable by a force. The force can be supplied by at least one of a memory wire, a spring and a motor. The force can be triggered by the release signal.

Figure 26:
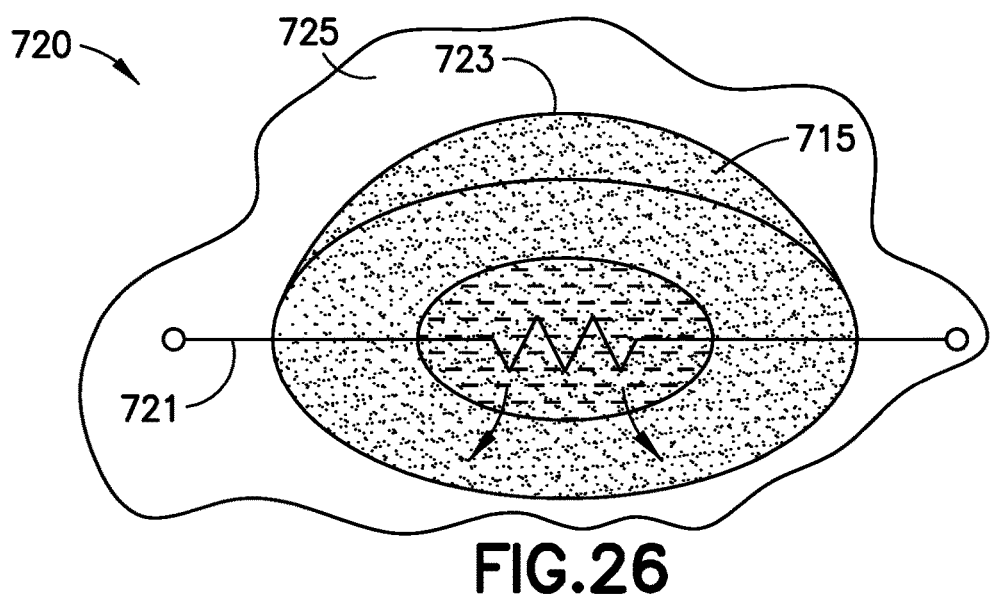
FIG. 26 depicts an illustrative embodiment of an adhesive removal apparatus of the present invention using a heat-released solvent.

FIG. 26 depicts an illustrative embodiment of an adhesive removal apparatus 720 using a heating element to release the solvent. The encapsulated solvent 721 is bonded over a micro-heating element 715 and a flow-hole 723 in the base of the device body 725. When a trigger signal is received, the micro-heating element 715 heats and ruptures a reservoir or encapsulations, allowing the solvent 721 to flow through the holes 723 to the adhesive. The heating element 715 is in direct contact with the encapsulation wall, and is small enough that the heating is not felt by the user.

In an illustrative embodiment of an adhesive removal apparatus, the adhesive solvent can be bonded over a micro-heating element heatable to rupture the at least one adhesive removal reservoir and release adhesive solvent. The micro-heating element can be activatable by the release signal.

FIG. 27 depicts an illustrative embodiment of an adhesive removal apparatus 730 using a dual stopper mechanism. The solvent is on board the device in a solvent reservoir 731, trapped between two stoppers 735 and 736. When the trigger signal is received, the force mechanism 740, such as a SMA wire or another memory wire, or a triggered spring, a triggered preloaded spring, and the like, pushes the assembly forward from a solvent containing position to a solvent releasing position where solvent can flow through a hole. Once the front stopper 735 is past the flow-hole, solvent is forced out and into contact with the adhesive pad for easy removal of the adhesive pad from the skin. Alternatively, only one or any number of stoppers can be used.

In an illustrative embodiment of an adhesive removal apparatus, the at least one adhesive solvent reservoir can include at least one stopper movable from a solvent containing position to a solvent releasing position where adhesive solvent flows through at least one hole. The at least one stopper can be movable by a force. The force can be supplied by at least one of a memory wire, a spring and a motor. The force can be triggered by a release signal.

FIG. 28 depicts an illustrative embodiment of an adhesive removal apparatus 750 using a squeeze chamber. As the user grips the device body 745 for removal, the user can push sides of the device body 745 together, breaking the internal ampule of adhesive solvent. For example, forces F' and F''' can press sides of the device body together, thus breaking an internal ampule of adhesive solvent 751, which then wicks to and releases the adhesive pad 755.

In an illustrative embodiment of an adhesive removal apparatus the at least one adhesive solvent reservoir can be disposed between two sides of the body of the device movable toward one another to break the at least one adhesive solvent reservoir and release adhesive solvent. The two sides are movable toward one another by a user gripping the body of the device.

FIG. 29 depicts an illustrative embodiment of an adhesive removal apparatus 760 using a twist chamber. As the user grips the device body 763 for removal, and can twist the device body, expelling adhesive solvent. For example, circular forces F''' associated with a slight twist of the device body 763 compress and break an internal chamber 761. This releases the solvent, which then wicks to and releases the adhesive pad 765.

In an illustrative embodiment of an adhesive removal apparatus, the body of the device can be twistable with respect to the at least one adhesive solvent reservoir to break the at least one adhesive solvent reservoir and release adhesive solvent. The body of the device can be twistable by a user.

Figure 30A:
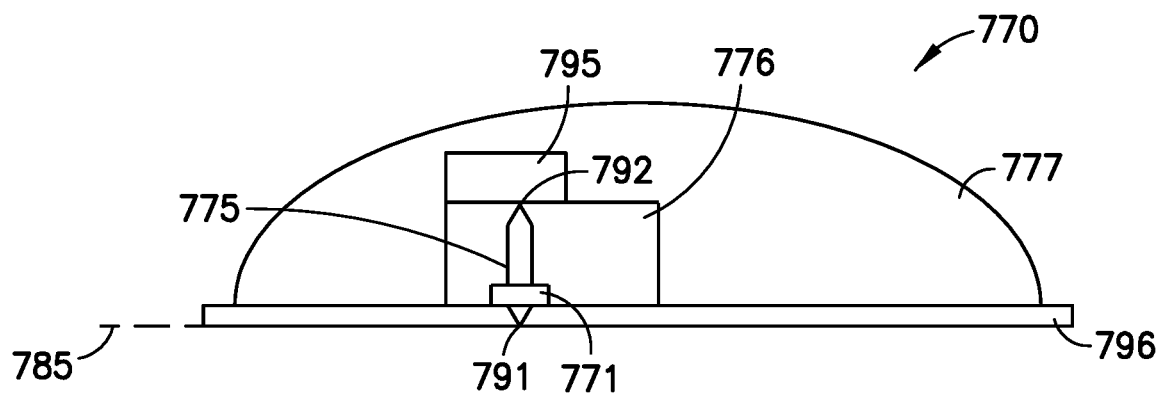
FIGS. 30a-30c depict illustrative embodiments of an adhesive removal apparatus of the present invention using motor activation.
Figure 30B:
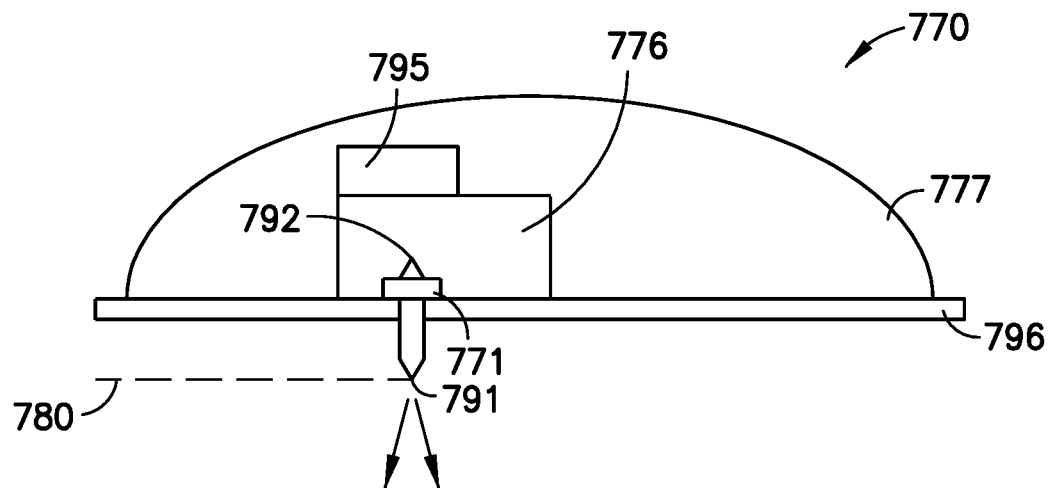
Figure 30C:
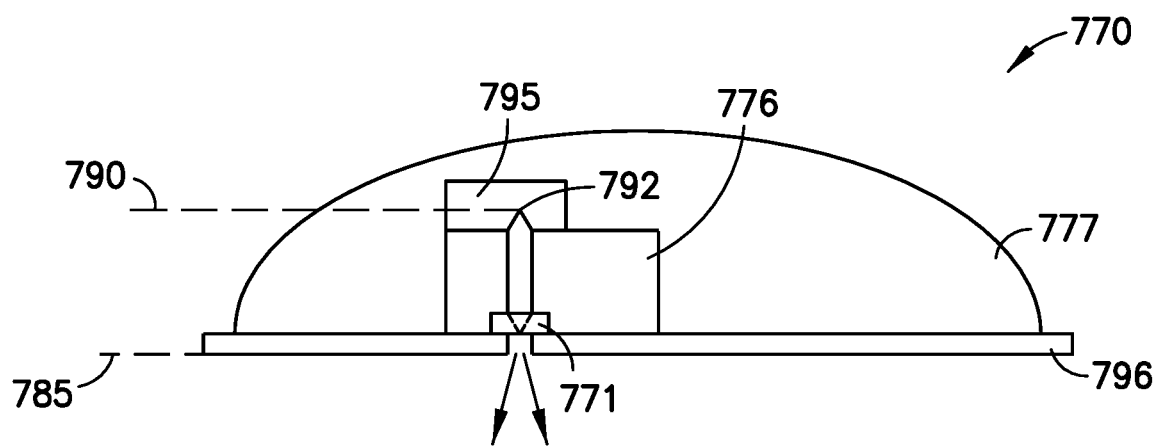

FIGS. 30a-30c depicts illustrative embodiments of an adhesive removal apparatus 770 using motor activation. This embodiment uses a motor 771 and wireless capability already onboard a patch pump. A local, remote, wired or wireless controller can signal to infuse, retract, or release adhesive solvent. A cannula 775 of a patch pump is inserted into a user to supply insulin from the insulin reservoir and mechanization 776 in the device body 777 of the patch pump during normal operation. Cannula 775 can include a double-ended shaft. When a signal is received to end therapy, a front end 791 of cannula 775 is retracted from an infusion position 780, beyond a home position 785, as a back end 792 of cannula 775 of the double-ended shaft 791 of the cannula 775 moves to a solvent expel position 790 and punctures the adhesive solvent reservoir 795, allowing the solvent to flow into contact with the adhesive pad 796.

In an illustrative embodiment of an adhesive removal apparatus, the device includes a medicament reservoir containing medicament, wherein the medicament reservoir can be disposed above the adhesive pad and the at least one adhesive solvent reservoir can be disposed above the medicament reservoir, and at least one cannula comprising a double-ended shaft with a front end and a back end, wherein the at least one cannula can be movable from a home position of the front end to an infusion position of the front end to a solvent expel position of the back end.

The individual components used in the exemplary patch pump embodiments disclosed herein, including pump engines, fluidic assemblies, metering systems, catheter deployment assemblies, fluid reservoirs and control systems, can be based on existing designs and technologies which are known in the art. For example, pump engines, fluidic assemblies and metering systems utilizing stepper motors, shape memory alloy (SMA) actuators, piezoelectric actuators, microelectromechanical systems (MEMS) devices, and directional control valves may be used. Fluid reservoirs may be rigid or deformable (e.g., with force applied by a movable plunger or preloaded spring).

The following U.S. and foreign patent documents, which are incorporated by reference herein, disclose exemplary components and subsystems which may be used in the practice of the present invention:

| |
|---|
| U.S. Pat. No. 5,858,001 |
| U.S. Pat. No. 5,858,005 |
| U.S. Pat. No. 5,957,895 |
| U.S. Pat. No. 6,074,369 |
| U.S. Pat. No. 6,551,276 |
| U.S. Pat. No. 6,589,229 |
| U.S. Pat. No. 6,656,158 |
| U.S. Pat. No. 6,740,059 |
| U.S. Pat. No. 6,852,104 |
| U.S. Pat. No. 6,960,192 |
| U.S. Pat. No. 7,052,251 |
| U.S. Pat. No. 7,109,878 |
| U.S. Pat. No. 7,128,727 |
| U.S. Pat. No. 7,226,278 |
| U.S. Pat. No. 7,250,037 |
| U.S. Pat. No. 7,303,549 |
| U.S. Pat. No. 7,678,079 |
| U.S. Pat. No. 7,857,131 |
| US 2008/0097381 |
| US 2009/0048563 |
| US 2009/0062778 |
| EP 2019206 |

While certain exemplary embodiments of the present invention have been shown and described herein with reference to certain preferred embodiments thereof, it will be understood by those skilled in the art that various changes in form and details may be made therein without departing from the spirit and scope of the invention.

What is claimed is:

1. A method of on-body fluid delivery using a primary user interface communicatively couplable to a primary patch pump comprising a first reservoir adapted to contain a first fluid, a first cannula, a first pump adapted to infuse the first fluid from the first reservoir through the first cannula, and a first microcontroller adapted to control operations of the first pump,
the method comprising the steps of:
attaching a primary patch pump to a user's skin at an attachments site;
inserting the first cannula into the attachment site through a surface of the primary patch pump attached to the user's skin;
pairing the primary patch pump for remote wireless communication via a wireless communication interface to a primary user interface;
communicating via the wireless communication interface between the primary patch pump and the primary user interface to determine whether user instructions have been received at the primary user interface; and
if it is determined that user instructions have been received at the primary user interface:
sending machine instructions from the primary user interface to the primary patch pump via the wireless communication interface according to the user instructions; and
initiating a bolus dose or basal rate using the first microcontroller according to the machine instructions;
checking by the primary patch pump for an error condition;
if an error condition is detected by the primary patch pump, alerting a user via an alert mechanism and transferring relevant data from the primary patch pump to the primary user interface;
if no error condition is detected by the primary patch pump, transferring relevant data from the primary patch pump to the primary user interface, and returning to the step of the primary patch pump communicating with the primary user interface;
checking whether communication with the primary user interface was successful;
if communication with the primary user interface was not successful, deploying a second catheter from a second pump and continuing infusion with the second pump.

2. The method of on-body fluid delivery of claim 1, wherein an error condition comprises a condition indicative of at least one of a cannula occlusion, a low reservoir, an end of reservoir, a depleted battery, a battery failure, a cannula deployment, entrapped air and a leakage.

3. The method of on-body fluid delivery of claim 1, wherein relevant data comprise data indicative of at least one an infusion profile update, an infusion command, a bolus dose, a bolus dose requirement, a basal rate, a basal rate adjustment, a confirmation of delivery, an error state or condition, and a confirmation of adjustment.

4. The method of on-body fluid delivery of claim 1, wherein the primary user interface re-synchronizes the primary user interface and the primary patch pump.

5. The method of on-body fluid delivery of claim 4, wherein the primary user interface re-synchronizes the primary user interface and the primary patch pump using a real-time clock.

6. The method of on-body fluid delivery of claim 1, wherein pairing the primary patch pump to the primary user interface comprises assigning a first unique identifier to the primary user interface and a second unique identifier to the primary patch pump.

7. The method of on-body fluid delivery of claim 1, further comprising the step of:
entering a primary patch pump SNIFF mode for up to a predetermined primary patch pump SNIFF time to check for an error condition.

8. The method of on-body fluid delivery of claim 1, wherein the primary patch pump is attachable to skin.

9. The method of on-body fluid delivery of claim 1, wherein the first fluid comprises insulin.

10. The method of on-body fluid delivery of claim 1, further comprising the steps of:
entering a primary user interface SLEEP mode by the primary user interface and the primary patch pump;
entering a primary user interface WAKE mode by the primary user interface at predetermined primary user interface WAKE time intervals; and entering a primary patch pump WAKE mode by the primary patch pump at predetermined primary patch pump WAKE time intervals, wherein a power level associated with the primary user interface SLEEP mode is lower than a power level associated with a primary user interface WAKE mode, and wherein a power level associated with the primary patch pump SLEEP mode is lower than a power level associated with a primary patch pump WAKE mode.

11. The method of on-body fluid delivery of claim 10, wherein at least one of a SLEEP cycle, a WAKE cycle and a SNIFF cycle of the primary user interface is synchronized with at least one of a SLEEP cycle, a WAKE cycle and a SNIFF cycle of the primary patch pump.

12. The method of on-body fluid delivery of claim 10, wherein if the primary user interface is engaged for an adjustment of basal rate or a setting of bolus delivery, after the adjustment or setting at least one of a SLEEP cycle, a WAKE cycle and a SNIFF cycle of the primary user interface is synchronized with at least one of a SLEEP cycle, a WAKE cycle and a SNIFF cycle of the primary patch pump.

\* \* \* \* \*